US006914123B2

(12) United States Patent
Cochran et al.

(10) Patent No.: US 6,914,123 B2
(45) Date of Patent: Jul. 5, 2005

(54) HAIRPIN PEPTIDES WITH A NOVEL STRUCTURAL MOTIF AND METHODS RELATING THERETO

(75) Inventors: Andrea G. Cochran, San Francisco, CA (US); Melissa A. Starovasnik, San Francisco, CA (US); Nicholas Skelton, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 447 days.

(21) Appl. No.: 09/836,770

(22) Filed: Apr. 17, 2001

(65) Prior Publication Data

US 2003/0175799 A1 Sep. 18, 2003

(51) Int. Cl.$^7$ .................................................. C07K 7/00
(52) U.S. Cl. ..................... 530/326; 530/327; 530/325; 530/324; 530/300; 435/7.1
(58) Field of Search ............................... 530/326, 327, 530/325, 324, 300; 435/7.1

(56) References Cited

U.S. PATENT DOCUMENTS

| | | | |
|---|---|---|---|
| 4,833,092 A | 5/1989 | Geysen | |
| 5,223,409 A | 6/1993 | Ladner et al. | 435/69.7 |
| 5,534,615 A | 7/1996 | Baker et al. | 530/350 |
| 5,627,024 A | 5/1997 | Maruyama et al. | |
| 5,766,905 A | 6/1998 | Studier et al. | |
| 5,821,047 A | 10/1998 | Garrard et al. | |
| 5,824,483 A | 10/1998 | Houston, Jr. et al. | |
| 5,830,851 A | 11/1998 | Wrighton et al. | |
| 5,866,341 A | 2/1999 | Spinella et al. | 435/71 |
| 5,885,780 A | 3/1999 | Olivera et al. | 435/7.1 |
| 6,013,458 A | 1/2000 | Kahn et al. | 435/7.1 |
| 6,180,343 B1 | 1/2001 | Anderson et al. | |
| 6,475,806 B1 | 11/2002 | Benjamin et al. | 436/518 |
| 6,482,591 B2 | 11/2002 | Lockhart et al. | 435/6 |

FOREIGN PATENT DOCUMENTS

| | | |
|---|---|---|
| WO | WO 92/00091 | 1/1992 |
| WO | WO 94/03494 | 2/1994 |
| WO | WO 95/01800 | 1/1995 |
| WO | WO 95/34683 | 12/1995 |
| WO | WO 97/29185 | 8/1997 |
| WO | WO 98/49168 | 11/1998 |
| WO | WO 99/51625 | 10/1999 |
| WO | WO 00/20574 | 4/2000 |
| WO | WO 00/77194 | 12/2000 |

OTHER PUBLICATIONS

Barthe et al., Synthesis and NMR solution structure of an α–helical hairpin stapled with two disulfide bridges, *Protein Science*, 133:942–955 (2000) (abstract only).
Blanco, F. et al., "NMR Evidence of a Short Linear Peptide That Folds into a β–Hairpin in Aqueous Solution," *J. Am. Chem. Soc.*, 115(13):5887–5888 (1993).
Chou, P. et al., "Empirical Predictions Of Protein Conformation," *Ann. Rev. Biochem.*, 47:251–276 (1978).
Cochran, A., "Antagonists of protein–protein interactions", *Chemistry and Biology*, 7(4):R85–R94 (Apr. 2000).
Constantine, K. et al., "Structural and Dynamic Properties of a β–Hairpin–Forming Linear Peptide. 1. Modeling Using Ensemble–Averaged Constraints," *J. Am. Chem. Soc.*, 117(44):10841–10854 (1995).
Cwirla et al., "Peptide agonist of the thrombopoietin receptors as potent as the natural cytokine", *Science*, 276(5319):1696–1699 (Jun. 13, 1997).
de Alba, E. et al., "Conformational investigation of designed short linear peptides able to fold into β–hairpin structures in aqueous solution," *Folding & Design*, 1(2):133–144 (Feb. 26, 1996).
de Alba, E. et al., "Cross–strand side–chain interactions versus turn conformation in β–hairpins," *Protein Science*, 6:2548–2560 (1997).
de Alba, E. et al., "Interactions responsible for the pH dependence of the β–hairpin conformational population formed by a designed linear peptide," *Eur. J. Biochem.*, 233:283–292 (1995).
de Alba, E. et al., "Turn Residue Sequence Determines β–Hairpin Conformation in Designed Peptides," *J. Am. Chem. Soc.*, 119(1):175–183 (1997).
Domingo et al., "Synthesis of a mixture of cyclic peptides based on the Bowman–Birk reactive site loop to screen for serine inhibitors", *International Journal of Protein and Peptide Research*, 46:79–87 (1995).
Fairbrother et al., "Novel Peptides Selected to Bind Vascular Endothelial Growth Factor Target the Receptor–Binding State", *Biochemistry*, 37:17754–17764 (1998).
Falcomer et al., "Chain Reversals in Model Peptides: Studies of Cystine–Containing Cyclic Peptides. 3. Conformational Free Energies of Cyclization of Tetrapeptides of Sequence Ac–Cys–Pro–X–Cys–NHMe", *J. Am. Chem. Soc.*, 114:4036–4042 (1992).
Favre et al., "Structural Mimicry of Canonical Conformations in Antibody Hypervariable Loops Using Cyclic Peptides Containing a Heterochiral Diproline Template", *J. Am. Chem. Soc.*, 121:2679–2685 (1999).

(Continued)

*Primary Examiner*—T. D. Wessendorf
(74) *Attorney, Agent, or Firm*—Merchant & Gould P.C.

(57) ABSTRACT

The invention is directed to a model system for structure-activity relationship analysis of peptide or protein molecules involved in important biological processes. Provided by the invention are combinatorial peptide libraries comprising peptides with a novel "tryptophan zipper" scaffold (trpzip) that forms stable β-hairpin structure in solution. Methods of selecting and using such scaffold are provided herein, which are useful for mimicking native protein structures and interactions and designing therapeutic agents. Thus, the invention has profound utility for biological studies and drug development.

6 Claims, 6 Drawing Sheets

OTHER PUBLICATIONS

Friedrichs, M. et al., "Structural and Dynamic Properties of a β–Hairpin–Forming Linear Peptide. 2. $^{13}$C NMR Relaxation Analysis," *J. Am. Chem. Soc*, 117(44):10855–10864 (1995).

Griffiths–Jones, S. et al., "Dissecting the Stability of a β–Hairpin Peptide that Folds in Water: NMR and Molecular Dynamics Analysis of the β–Turn and β–Strand Contributions to Folding," *J. Mol. Biol.*, vol. 292, pp. 1051–1069 (1999).

Griffiths–Jones, S. et al., "NMR evidence for the nucleation of a β–hairpin peptide conformation in water by an Asn–Gly type I' β–turn sequence," *Chem. Commun.*, pp. 789–790 (1998).

Haque, T. et al., "Insights on β–Hairpin Stability in Aqueous Solution from Peptides with Enforced Type I' and Type II'β–Turns," *J. Am. Chem. Soc.*, 119:2303–2304 (1997).

Hutchinson, E. et al., "Determinants of strand register in antiparallel β–sheets of proteins," *Protein Science*, 7:2287–2300 (1998).

Kieber–Emmons et al., "Therapeutic peptides and peptidomimetics", *Current Opinion in Biotechnology*, 8(4):435–441 (Aug. 1997).

Kim, C. et al., "Thermodynamic β–sheet propensities measured using a zinc–finger host peptide," *Nature*, 362:267–270 (Mar. 18, 1993).

Kobayashi, N. et al., "Fragment Reconstitution of a Small Protein: Disulfide Mutant of a Short C–Terminal Fragment Derived from Streptococcal Protein G," *Biochemistry*, 38(11):3228–3234 (1999).

Kobayashi, N. et al., "Role of Side–chains in the Cooperative β–Hairpin Folding of the Short C–Terminal Fragment Derived from Streptococcal Protein G," *Biochemistry*, 39(21):6564–6571 (2000).

Ladner, R., Constrained peptides as binding entitites, *TIBTECH*, 13:426–430 (Oct. 1995).

Lin and Kim, "Urea Dependence of Thiol–Disulfide Equilibria in Thioredoxin: Confirmation of the Linkage Relationship and a Sensitive Assay for Structure", *Biochemistry*, 28(12):5282–5287 (1989).

Livnah et al., "Functional mimicry of a protein hormone by a peptide agonist: the EPO receptor complex at 2.8 A", *Science*, 273(5274):464–471 (Jul. 26, 1996).

Lowman et al., "Molecular mimics of insulin–like growth factor 1 (IGF–1) for inhibiting IGF–1: IGF–binding protein interactions", *Biochemistry*, 37(25):8870–8878 (Jun. 23, 1998).

Mattos, C. et al., "Analysis of Two–residue Turns in Proteins," *J. Mol. Biol.*, 238:733–747 (1994).

Maynard, A. et al., "NMR structural analysis of a β–hairpin peptide designed for DNA binding," *Chem. Commun.*, pp. 1297–1298 (1997).

Maynard, A. et al., "Origin of β–Hairpin Stability in Solution: Structural and Thermodynamic Analysis of the Folding of a Model Peptide Supports Hydrophobic Stabilization in Water," *J. Am. Chem. Soc.*, 120(9):1996–2007 (1998).

Milburn et al., "Chain reversals in model peptides: studies of cystine–containing cyclic peptides. II. Effects of valyl residues and possible i–to–(i +3) attractive ionic interactions on cyclization of [Cys$^1$], [Cys$^6$] hexapeptides", *International Journal of Peptide & Protein Research*, 31(3):311–321 (Mar. 1988).

Minor, Jr., D. et al., "Context is a major determinant of β–sheet propensity," *Nature*, 371:264–267 (Sep. 15, 1994).

Muñoz, V. et al., "Intrinsic Secondary Structure Propensities of the Amino Acids, Using Statistical φ–Ψ Matrices: Comparison With Experimental Scales," *Proteins: Structure, Function, and Genetics*, 20:301–311 (1994).

Ried, C. et al., "High Affinity Endotoxin–binding and Neutralizing Peptides Based on the Crystal Structure of Recombinant *Limulus* Anti–lipopolysaccharide Factor," *Journal of Biological Chemistry*, 271(45):28120–28127 (Nov. 8, 1996).

Rohrer, S. et al., "Rapid Identification of Subtype–Selective Agonists of the Somatostatin Receptor Through Combinatorial Chemistry," *Science*, 282:737–740 (Oct. 23, 1998).

Searle, M. et al., "A short linear peptide derived from the N–terminal sequence of ubiquitin folds into a water–stable non–native β–hairpin," *Nature Structural Biology*, 2(11):999–1006 (Nov. 1995).

Smith, C. et al., "A Thermodynamic Scale for the β–Sheet Forming Tendencies of the Amino Acids," *Biochemistry*, 33(18):5510–5517 (1994).

Smith, C. et al., "Guidelines for Protein Design: The Energetics of βSheet Side Chain Interactions," *Science*, 270:980–982 (Nov. 10, 1995).

Stroup and Gierasch, "Reduced Tendency to Form a βTurn in Peptides from the P22 Tailspike Protein Correlates with a Temperature–Sensitive Folding Defect", *Biochemistry*, 29:9765–9771 (1990).

Syud, F. et al., "Interstrand Side Chain–Side Interactions in a Designed β–Hairpin: Significance of Both Lateral and Diagonal Pairings," *J. Am. Chem. Soc.*, 123(36):8667–8677 (2001).

Wiesmann et al., "Crystal Structure of the Complex between VEGF and a Receptor–Blocking Peptide", *Biochemistry*, 37:17765–17772 (1998).

Wouters, M. et al., "An Analysis of Side Chain Interactions and Pair Correlations Within Antiparallel β–Sheets: The Difference Between Backbone Hydrogen–Bonded and Non–Hydrogen–Bonded Residue Pairs," *Proteins: Structure, Function, and Genetics*, 22:119–131 (1995).

Wrighton et al., "Small peptides as potent mimetrics of the protein hormone erythropoietin", *Science*, 273:458–463 (Jul. 26, 1996).

Alexander et al., "Thermodynamic Analysis of the Folding of the Streptococcal Protein G IgG–Binding Domains B1 and B2: Why Small Proteins Tend to Have High Denaturation Temperatures" *Biochemistry* 31:3597–3603 (1992).

Allen et al., "Finding prospective partners in the library: the two–hybrid system and phage display find a match" *TIBS* 20:511–516 (1995).

Ball et al., "Conformational Constraints: Nonpeptide β–Turn Mimics" *Journal of Molecular Recognition* 3(2):55–64 (1990).

Barbas, "Recent advances in phage display" *Current Opinion in Biotechnology* 4:526–530 (1993).

Bass et al., "Hormone Phage An Enrichment Method for Variant Proteins with Altered Binding Properties" *Proteins: Structure, Function, and Genetics* 8(4):309–314 (1990).

Becktel and Schellman, "Protein Stability Curves" *Biopolymers* 26:1859–1877 (1987).

Bianchi et al., "A Conformationally Homogeneous Combinatorial Peptide Library", *J. Mol. Biol.* 247:154–160 (1995).

Bianchi et al., "High level expression and rational mutagenesis of a designed protein, the minibody. From an insoluble to a soluble molecule" *Journal of Molecular Biology* 236(2):649–659 (Feb. 18, 1994).

Blanco et al., "A short linear peptide that folds into a native stabel B–hairpin in aqueous solution" *Structural Biology* 1(9):584–590 (Sep. 1994).

Bradbury and Cattaneo, "The use of phage display in neurobiology" *Trends in Neuroscience* 18:243–249 (1995).

Choo and Klug, "Designing DNA–binding proteins on the surface of filamentous phage" *Current Opinion in Biotechnology* 6:431–436 (1995).

Chothia, "Coiling of B–Pleated Sheets" *J. Mol. Biol.* 163:107–117 (1983).

Christmann et al., "The cystine knot of a squash–type protease inhibitor as a structural scaffold for *Escherichia coli* cell surface display of conformationally constrained peptides" *Protein Engineering* 12(9):797–806 (Sep. 1999).

Clackson and Wells, "In vitro selection from protein and peptide libraries" *Trends Biotechnol.* 12:173–184 (1994).

Clackson et al., "Making antibody fragments using phage display libraries" *Nature* 352:624–628 (1991).

Cochran et al., "A Minimal Peptide Scaffold for B–Turn Display: Optimizing a Strand Position in Disulfide–Cyclized B–Hairpins" *J. Am. Chem. Soc.* 123:625–632 (2001).

Cortese et al., "Identification of biologically active peptides using random libraries displayed on phage" *Current Opinion in Biotechnology* 6:73–80 (1995).

Cortese et al., "Selection of biologically active peptides by phage display of random peptide libraries" *Current Opinion in Biotechnology* 7:616–621 (1996).

Cunningham and Wells, "High–Resolution Epitope Mapping of hGh–Receptor Interactions by Alanine–Scanning Mutagenesis" *Science* 244:1081–1085 (1989).

Cwirla et al., "Peptides on phage: a vast library of peptides for identifying ligands" *Proc. Natl. Acad. Sci. USA* 87(16):6378–6382 (1990).

Dunn, I.S., "Phage display of proteins" *Current Opinion in Biotechnology* 7:547–553 (1996).

Efimov et al., "Bacteriophage T4 as a Surface Display Vector" *Virus Genes* 10(2):173–177 (1995).

Espinosa and Gellman, "A Designed B–Hairpin Containing a Natural Hydrophobic Cluster" *Agnew. Chem. Int. Ed.* 39(13):2330–2333 (2000).

Felici, "Selection of antibody ligands from a large library of oligopeptide expressed on a multivalent exposition vector" *J. Mol. Biol.* 222:301–310 (1991).

Fowlkes et al., "Multipurpose Vectors for Peptide Expression on the M13 Viral Surface" *BioTechniques* 13(3):422–427 (1992).

Gill and von Hippel, "Calculation of Protein Extinction Coefficients from Amino Acid Sequence Data" *Analytical Biochemistry* 182:319–326 (1989).

Gram et al., "In vitro selection and affinity maturation of antibodies from a naive combinatorial immunoglobulin library" *Proc. Natl. Acad. Sci. USA* 89(8):3576–3580 (Apr. 15, 1992).

Greenwood et al., "Peptides from Plasmodium falciparum Circumsporozoite Protein as Antigens" *J. Mol. Bio.* 220:821–827 (1991).

Gururaja et al., "A novel artificial loop scaffold for the noncovalent constraint of peptides" *Chem. & Biol.* 7:515–527 (2000).

Havel, "An Evaluation of Computational Strategies For Use In The Determination of Protein Structure From Distance Constraints Obtained By Nuclear Magnetic Resonance" *Prog. Biophys. molec. Biol.* 56:43–78 (1991).

Hogrefe et al., "Cloning in a bacteriophage lambda vector for the display of binding proteins on filamentous phage" *Gene* 137:85–91 (1993).

Honda et al., "Thermodynamics of a B–Hairpin Structure: Evidence for Cooperative Formation of Folding Nucleus" *J. Mol. Biol.* 295:269–278 (2000).

Hoogenboom et al., "Multi–subunit proteins on the surface of filamentous phage: methodologies for displaying antibody (Fab) heavy and light chains" *Nucleic Acids Research* 19(15):4133–4137 (1991).

Iannolo et al., "Modifying Filamentous Phage Capsid: Limits in the Size of the Major Capsid Protein" *J. Mol. Biol.* 248:835–844 (1995).

Jiang et al., "Display of a PorA peptide from Neisseria meningitidis on the bacteriophage T4 capsid surface" *Chemical Abstracts* (Abstract No. 44380q) 128(5):147 (1998).

Johnson et al., "Analysis of Data From The Analytical Ultracentrifuge By Nonlinear Least–Squares Techniques" *Biophys. J.* 36:575–588 (Dec. 1981).

Kang et al., "Linkage of recognition and replication functions by assembling combinatorial antibody Fab libraries along phage surfaces" *Proc. Natl. Acad. Sci. USA* 88:4363–4366 (1991).

Karle et al., "Cyclic Cystine Peptides. Antiparallel B–Sheet Conformation for the 20–Membered Ring in Boc–Cys–Val–Aib–Ala–Leu–Cys–NHMe" *American Chemical Society* 110:1958–1963 (1988).

Kessler et al., "Peptide Conformations. 42. Conformation of Side Chains in Peptides Using Heteronuclear Coupling Constants Obtained by Two–Dimensional NMR Spectroscopy" *J. Am. Chem. Soc.* 109:6927–6933 (1987).

Kortemme et al., "Design of a 20–Amino Acid, Three–Stranded B–Sheet Protein" *Science* 281:253–256 (Jul. 10, 1998).

Lam et al., "A new type of synthetic peptide library for identifying ligand–binding activity" *Nature* 354:82–84 (1991).

Lindqvist and Naderi, "Peptide presentation by bacteriophage P4" *FEMS Microbiology Reviews* 17:33–39 (1995).

Lowman and Wells, "Monovalent Phage Display: A Method for Selecting Variant Proteins from Random Libraries" *Methods: Comp. to Methods Enzymol.* 3:205–216 (1991).

Lowman et al., "Selecting High–Affinity Binding Proteins by Monovalent Phage Display" *Biochemistry* 30(45):10832–10838 (1991).

Makowski, L., "Structural constraints on the display of foreign peptides on filamentous bacteriophages" *Gene* 128:5–11 (1995).

Malik and Perham, "New vectors for peptide display on the surface of filamentous bacteriophage" *Gene* 171:49–51 (1996).

Markland et al., "Design, construction and function of a multicopy display vector using fusions to the major coat protein of bacteriophage M13" *Gene* 109:13–19 (1991).

Marks et al., "By–passing immunization: human antibodies from V–gene libraries displayed on phage" *J. Mol. Biol.* 222:581–597 (1991).

Martin et al., "The affinity–selection of a minibody polypeptide inhibitor of human interleukin–6" *EMBO Journal* 13(22):5303–5309 (Nov 15, 1994).

McBride et al., "Selection of Chymotrypsin Inhibitors from a Conformationally–constrained Combinatorial Peptide Library" *Journal of Molecular Biology* 259(4):819–827 (Jun. 21, 1996).

McCafferty et al., "Phage antibodies: filamentous phage displaying antibody variable domains" *Nature* 348:552–554 (1990).

McGregor, "Selection of proteins and peptides from libraries displayed on filamentous bacteriophage" *Molecular Biotechnology* 6:155–162 (1996).

McLafferty et al., "M13 bacteriophage displaying disulfide–constrained microproteins" *Gene* 128:29–36 (1993).

Merrifield, R.B., "Solid Phase Peptide Synthesis. I. The Synthesis of a Tetrapeptide" *J. Am. Chem. Soc.* 85:2149–2154 (1963).

Milburn et al., "Chain Reversals in Model Peptides: Studies of Cystine–Containing Cyclic Peptides 1. Conformational Free Energies of Cyclization of Hexapeptides of Sequence Ac–Cys–X–Pro–Gly–Y–Cys–NHMe" *J. Am. Chem. Soc.* 109:4486–4496 (1987).

Milner–White, E., "Predicting the biologically active conformations of short polypeptides" *Trends in Pharmacological Sciences* 10(2):70–74 (Feb 1989).

Minor and Kim, "Measurement of the B–sheet–forming propensities of amino acids" *Nature* 367:660–663 (Feb. 17, 1994).

Munoz et al., "Folding dynamics and mechanism of B–hairpin formation" *Nature* 390:196–199 (Nov. 13, 1997).

Myszka and Chaiken, "Design and characterization of an intramolecular antiparallel coiled coil peptide" *Biochemistry* 33(9):2363–2372 (Mar 8, 1994).

Nygren and Uhlen, "Scaffolds for engineering novel binding sites in proteins" *Current Opinion in Structural Biology* 7(4):463–469 (Aug. 1997).

O'Boyle et al., "Identification of a novel peptide substrate of HSV–1 protease using substrate phage display" *Virology* 236:338–347 (1997).

O'Neil and Hoess, "Phage display: protein engineering by directed evolution" *Current Opinion in Structural Biology* 5:443–449 (1995).

Privalov and Gill, "Stability of Protein Structure and Hydrophobic Interaction" *Advances in Protein Chemistry* 39:191–243 (1988).

Ramirez–Alvarado et al., "B–Hairpin and B–Sheet Formation in Designed Linear Peptides" *Bioorganic & Medicinal Chemistry* 7:93–103 (1999).

Ramirez–Alvarado et al., "Conformational analysis of peptides corresponding to all the secondary structure elements of protein L B1 domain: Secondary structure propensities are not conserved in proteins with the same fold" *Protein Science* 6:162–174 (1997).

Ramirez–Alvarado et al., "De novo design and structural analysis of a model B–hairpin peptide system" *Nature Structural Biology* 3(7):604–612 (Jul. 1996).

Ramirez–Alvarado et al., "Role of B–Turn Residues in B–Hairpin Formation and Stability in Designed Peptides" *J. Mol. Biol.* 273:898–912 (1997).

Ren et al., "Cloning of linear DNAs in vivo by overexpressed T4 DNA ligase: construction of a T4 phage hoc gene display vector" *Chemical Abstracts* (Abstract No. 215644q) 127(16):155 (1997).

Ren et al., "Phage display of intact domains at high copy number: A system based on SOC, the small outer capsid protein of bacteriophage T4" *Protein Science* 5:1833–1843 (1996).

Ren et al., "Phage T4 SOC and HOC display of biologically active, full–length proteins on the viral capsid" *Gene* 215:439–444 (1998).

Rietman et al., "The solution structure of the synthetic circular peptide CGVSRQGKPYC NMR studies of the folding of a synthetic model for the DNA–binding loop of the ssDNA–binding protein encoded by gene V of phage M13" *European Journal of Biochemistry* 238:706–713 (1996).

Russell and Cochran, "Designing Stable B–Hairpins: Energetic Contributions from Cross–Strand Residues" *J. Am. Chem. Soc.* 122:12600–12601 (2000).

Scott and Smith, "Searching for peptide ligands with an epitope library" *Science* 249:386–390 (1990).

Sibanda et al., "Conformation of B–Hairpins in Protein Structures" *J. Mol. Biol.* 206:759–777 (1989).

Skelton et al., "Determination of the Solution Structure of the Peptide Hormone Guanylin: Observation of a Novel Form of Topological Stereoisomerism" *Biochemistry* 33:13581–13592 (1994).

Smith and Pease, "Reverse turns in peptides and proteins" *CRC Critical Reviews in Biochemistry* 8(4):315–399 (1980).

Smith and Scott, "Libraries of Peptides and Proteins Displayed on Filamentous Phage" *Methods in Enzymology* 217:228–257 (1993).

Smith et al., "Small binding proteins selected from a combinatorial repertoire of knottins displayed on phage" *Journal of Molecular Biology* 277(2):317–332 (Mar. 27, 1998).

Smith, "Surface display and peptide libraries" *Gene* 128:1–2 (1993).

Smith, G. P., "Surface presentation of protein epitopes using bacteriophage expression systems" *Curr. Opin. Biotechnol.* 2(5):668–673 (1991).

Soumillion et al., "Phage display of enzymes and in vitro selection for catalytic activity" *Applied Biochemistry and Biotechnology* 47:175–190 (1994).

Stranger and Gellman, "Rules for Antiparallel B–Sheet Design: D–Pro–Gly Is Superior to L–Asn–Gly for B–Hairpin Nucleation" *J. Am. Chem. Soc.* 120:4236–4237 (1998).

Syud et al., "NMR–Based Quantification of B–Sheet Populations in Aqueous Solution through Use of Reference Peptides for the Folded and Unfolded States" *J. Am. Chem. Soc.* 121:11577–11578 (1999).

Thennarasu and Nagaraj, "Synthetic Peptides Corresponding to the B–Hairpin Loop of Rabbit Defensin NP–2 Show Antimicrobial Activity" *Biochem. & Biophys. Res. Comm.* 254:281–283 (1999).

Vita et al., "Novel miniproteins engineered by the transfer of active sites to small natural scaffolds" *Biopolymers* 47(1):93–100 (1998).

Vita et al., "Rational engineering of a miniprotein that reproduces the core of the CD4 site interacting with HIV–1 envelope glycoprotein" *Proc. Natl. Acad. Sci. USA* 96(23):13091–13096 (Nov. 9, 1999).

Walse et al., "Structure of a cyclic peptide with a catalytic triad, determined by computer simulation and NMR spectroscopy" *J. Comput Aided Mol Des* 10:11–22 (1996).

Wells et al., "Cassette Mutagenesis: an Efficient Method for Generation of Multiple Mutations at Defined Sites" *Gene* 34(2–3):315–323 (1985).

Zerella et al., "Autonomous folding of a peptide corresponding to the N-terminal B-hairpin from ubiquitin" *Protein Science* 8:1320–1331 (1999).

Zerella et al., "Structural characterization of a mutant peptide derived from ubiquitin: Implications for protein folding" *Protein Science* 9:2142–2150 (2000).

Zhang et al., "Synthetic CD4 exocyclic peptides antagonize CD4 holoreceptor binding and T cell activation" *Nature Biotechnology* 14:472–475 (Apr. 1996).

Zhang et al., "Synthetic CD4 exocyclics inhibit binding of human immunodeficiency virus type 1 envelope to CD4 and virus replication in T lymphocytes" *Nature Biotechnology* 15(2):150–154 (Feb. 1997).

Zhong, "Conformational Mimicry of a Chlamydial Neutralization Epitope on Filamentous Phage" *Journal of Biological Chemistry* 269:24183–24188 (1994).

Zoller and Smith, "Oligonucleotide–directed Mutagenesis Using M13–derived Vectors: An Efficient and General Procedure for the Production of Point Mutations in Any Fragment of DNA" *Nucl. Acids Res.* 10(20):6487–6500 (1982).

SEQUENCE LISTING

<160> NUMBER OF SEQ ID NOS: 16

<210> SEQ ID NO 1
<211> LENGTH: 12
<212> TYPE: PRT
<213> ORGANISM: Artificial Sequence

```
<220> FEATURE:
<223> OTHER INFORMATION: Peptide

<400> SEQUENCE: 1

Ser Trp Thr Trp Glu Gly Asn Lys Trp Thr Trp Lys
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: Peptide

<400> SEQUENCE: 2

Ser Trp Thr Trp Glu Asn Gly Lys Trp Thr Trp Lys
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Peptide; Pro at position 6 is D-Pro

<400> SEQUENCE: 3

Ser Trp Thr Trp Glu Pro Asn Lys Trp Thr Trp Lys
 1               5                  10

<210> SEQ ID NO 4
<211> LENGTH: 16
<212> TYPE: PRT
<213> ORGANISM: Streptococcus
<220> FEATURE:
<221> NAME/KEY: Streptococcus
<222> LOCATION: Full
<223> OTHER INFORMATION: The 41-56 residue fragment of the protein G B1
      domain

<400> SEQUENCE: 4

Gly Glu Trp Thr Tyr Asp Asp Ala Thr Lys Thr Phe Thr Val Thr
 1               5                  10                  15
Glu

<210> SEQ ID NO 5
<211> LENGTH: 16
<212> TYPE: PRT
<213> ORGANISM: Artificial Sequence
<220> FEATURE:
<223> OTHER INFORMATION: Peptide

<400> SEQUENCE: 5

Gly Glu Trp Thr Trp Asp Asp Ala Thr Lys Thr Trp Thr Trp Thr
 1               5                  10                  15
Glu

<210> SEQ ID NO 6
<211> LENGTH: 16
<212> TYPE: PRT
<213> ORGANISM: Artificial Sequence
<220> FEATURE:
<223> OTHER INFORMATION: Peptide
```

-continued

```
<400> SEQUENCE: 6

Gly Glu Trp Thr Tyr Asp Asp Ala Thr Lys Thr Phe Thr Trp Thr
 1               5                  10                  15
Glu

<210> SEQ ID NO 7
<211> LENGTH: 16
<212> TYPE: PRT
<213> ORGANISM: Artificial Sequence
<220> FEATURE:
<223> OTHER INFORMATION: Peptide

<400> SEQUENCE: 7

Gly Glu Trp Thr Trp Asp Asp Ala Thr Lys Thr Trp Thr Val Thr
 1               5                  10                  15
Glu

<210> SEQ ID NO 8
<211> LENGTH: 16
<212> TYPE: PRT
<213> ORGANISM: Artificial Sequence
<220> FEATURE:
<223> OTHER INFORMATION: Peptide

<400> SEQUENCE: 8

Gly Glu Trp His Trp Asp Asp Ala Thr Lys Thr Trp Val Trp Thr
 1               5                  10                  15
Glu

<210> SEQ ID NO 9
<211> LENGTH: 16
<212> TYPE: PRT
<213> ORGANISM: Artificial Sequence
<220> FEATURE:
<223> OTHER INFORMATION: Peptide

<400> SEQUENCE: 9

Gly Glu Trp Val Trp Asp Asp Ala Thr Lys Thr Trp His Trp Thr
 1               5                  10                  15
Glu

<210> SEQ ID NO 10
<211> LENGTH: 16
<212> TYPE: PRT
<213> ORGANISM: Artificial Sequence
<220> FEATURE:
<223> OTHER INFORMATION: Peptide

<400> SEQUENCE: 10

Gly Glu Trp Val Trp Asp Asp Ala Thr Lys Thr Trp Val Trp Thr
 1               5                  10                  15
Glu

<210> SEQ ID NO 11
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (2)
<223> OTHER INFORMATION: Xaa can be any amino acid
```

```
<220> FEATURE:
<221> NAME/KEY: MISC_FEATURE
<222> LOCATION: (5)
<223> OTHER INFORMATION: Xaa can be any amino acid

<400> SEQUENCE: 11

Cys Xaa Pro Gly Xaa Cys
  1               5

<210> SEQ ID NO 12
<211> LENGTH: 11
<212> TYPE: PRT
<213> ORGANISM: Artificial Sequence
<220> FEATURE:
<223> OTHER INFORMATION: Peptide

<400> SEQUENCE: 12

Cys Gly Val Ser Arg Gln Gly Lys Pro Tyr Cys
  1               5                  10

<210> SEQ ID NO 13
<211> LENGTH: 18
<212> TYPE: PRT
<213> ORGANISM: Artificial Sequence
<220> FEATURE:
<223> OTHER INFORMATION: Peptide

<400> SEQUENCE: 13

Cys Ala Gly Phe Met Arg Ile Arg Gly Arg Ile His Pro Leu Cys Met Arg Arg
  1               5                  10                  15

<210> SEQ ID NO 14
<211> LENGTH: 6
<212> TYPE: PRT
<213> ORGANISM: Artificial Sequence
<220> FEATURE:
<223> OTHER INFORMATION: Peptide

<400> SEQUENCE: 14

Ser Trp Thr Trp Glu Gly
  1               5

<210> SEQ ID NO 15
<211> LENGTH: 6
<212> TYPE: PRT
<213> ORGANISM: Artificial Sequence
<220> FEATURE:
<223> OTHER INFORMATION: Peptide

<400> SEQUENCE: 15

Asn Lys Trp Thr Trp Lys
  1               5

<210> SEQ ID NO 16
<211> LENGTH: 4
<212> TYPE: PRT
<213> ORGANISM: Artificial Sequence
<220> FEATURE:
<223> OTHER INFORMATION: Peptide

<400> SEQUENCE: 16

Glu Gly Asn Lys
  1
```

HAIRPIN PEPTIDES WITH A NOVEL STRUCTURAL MOTIF AND METHODS RELATING THERETO

FIELD OF THE INVENTION

The present invention relates in general to protein chemistry, and more specifically to the identification and characterization of a novel small peptide motif with stable conformation, as well as to libraries of conformationally-constrained peptides and methods of generating and screening such libraries for biological and pharmaceutical uses.

BACKGROUND OF THE INVENTION

Structure-Activity Relationship (SAR) studies provide valuable insights for understanding intermolecular interactions between bioactive molecules. In their natural states, bioactive molecules often adopt unique, conformationally-constrained structures in order to recognize and bind to their binding partners, to form a molecular complex therewith, and in turn to elicit specific activities. In particular, protein-protein interactions are crucial events involved in most biological and pathological processes, and are therefore logical targets for drug design. Important protein-protein interactions occur between such binding partners as enzyme-substrate, ligand-receptor, and antigen-antibody complexes.

One of the revolutionary advances in drug discovery is the development of combinatorial libraries. Combinatorial libraries are collections of different molecules, such as peptides, that can be made synthetically or recombinantly. Member peptides in a combinatorial peptide library include amino acids incorporated randomly into certain or all positions of their sequences. Such libraries have been generated and used in various ways to screen for peptide candidates which bind effectively to target molecules and to identify such sequences.

Many methods for generating peptide libraries have been developed and described. For example, members of the peptide library can be created by split-synthesis performed on a solid support such as polystyrene or polyacrylamide resin, as described by Lam et al. (1991) *Nature* 354:82 and PCT publication WO 92/00091. The method disclosed by U.S. Pat. No. 4,833,092 involves the synthesis of peptides in a methodical and predetermined fashion, so that the placement of each library member peptide gives information concerning the synthetic structure of that peptide.

Phage display of peptide libraries has become a powerful tool for rapidly screening and identifying novel ligands of virtually any protein target. Of particular interests are display methods using filamentous bacteriophages. U.S. Pat. No. 5,821,047. This method allows the preparation of libraries as large as $10^{10}$–$10^{12}$ unique peptide members, many orders of magnitude larger than libraries that may be prepared synthetically. In addition to large library sizes, advantages of phage display include ease of library construction (Kunkel mutagenesis), coupling of the binding entity (displayed peptide) to a unique identifier (its DNA sequence), a selection protocol for amplifying rare binding clones in a pool, and the high fidelity of biosynthesis (compared to synthetic methods). Furthermore, rapid and inexpensive selection protocols are available for identifying those library members that bind to a target of interest. However, only natural peptides composed of L-amino acids may be displayed on phage, so the problem of defining three-dimensional structure-activity relationships is more difficult than it might be for a constrained peptidomimetic containing non-naturally occurring amino acids or nonpeptide components.

One possible solution to this problem is to use the structural constraints of a folded protein to present small variable peptide segments. Considerable effort has been devoted to introducing structural constraints into combinatorial peptide libraries so that the member peptides represent more closely their native states. Several protein scaffolds capable of presenting a sequence of interest in a conformationally-restricted fashion have been identified, including minibody structures (Bianchi et al. (1994) *J Mol Biol* 236:649–659), β sheets, coiled-coil stem structures (Myszka & Chaiken (1994) *Biochem* 33:2363–2372), zinc-finger domains, cysteine-linked (disulfide) structures, trans-glutaminase linked structures, cyclic peptides, helical barrels or bundles, leucine zipper motifs (Martin et al. (1994) *EMBO J* 13:5303–5309), etc.

A number of identified scaffolds have been used in the construction of combinatorial peptide libraries with structural constraints. U.S. Pat. No. 5,824,483 describes a synthetic peptide library containing peptides featuring α-helical conformation and thus capable of forming coiled-coil dimers with each other. McBride et al. (1996) *J Mol Biol* 259:819–827 describe a synthetic library of cyclic peptides mimicking the anti-tryptic loop region of an identified proteinase inhibitor. WO 00/20574 and U.S. Pat. No. 6,180,343B1 describe fusion constructs using scaffold proteins such as green fluorescent protein (GFP). Several small protein domains have also been proposed as peptide display scaffolds. Nygren & Uhlen (1997) *Curr. Opin. Struct. Biol.* 7:463–469; Vita et al. (1998) *Biopolymers* 47:93–100; Vita et al. (1999) *Proc. Natl. Acad. Sci. USA* 96:13091–13096; Smith et al. (1998) *J. Mol. Biol.* 277:317–332; Gururaja et al. (2000) *Chem. & Biol.* 7:515–527; Christmann et al. (1999) *Protein Engng.* 12:797–806.

Among the identified protein scaffolds, β-turns (hairpins) have been implicated as an important site for molecular recognition in many biologically active peptides. Smith & Pease (1980) *CRC Crit Rev Biochem* 8:315–300. Thus, peptides containing conformationally-constrained β-turns are particularly desirable. The great majority of the identified β-turn bearing peptides are cyclopeptides which have been generated by the cyclization of a peptide similar to a sequence in the natural substrate. Milner-White (1989) *Trends Pharmacol Sci* 10:70–74. These cyclopeptides, however, may still retain significant flexibility. For this reason, many studies have attempted to introduce rigid, nonpeptide compounds which mimic the β-turn. Peptides with such nonpeptide β-turn mimic provide useful leads for drug discovery. Ball & Alewood (1990) *J Mol Recog* 3:55–64; WO 94/03494. The structural mechanisms by which β-turns are stabilized, and specific strand registers are selected, continue to be the subject of considerable interest.

Several examples have been reported of disulfide-constrained peptides intended to mimic protein hairpins or as de novo designed hairpins. In many cases the design includes D-cysteines at one or both ends, as it was initially thought that disulfide bond geometry was not compatible with the cross-strand geometry of hairpins. However, there are some examples that do use L-cys. Evidence for structure is lacking in most studies of disulfide-cyclized peptides. Examples listed here are those whose structures have been experimentally determined, or that use no unusual amino acids and have potency close to a larger, hairpin-containing natural protein in a biological assay.

The structure of a hexapeptide (Boc-CL-Aib-AVC-NMe) was determined crystallographically, revealing a type II' turn and β-sheet geometry. Karle et al. *J. Am. Chem. Soc.* (1988) 110:1958–1963. An octapeptide with the same cysteine spacing was studied by NMR, and has a similar structure with a turn centered on Pro-Gly. Walse et al. (1996) *J. Comput.-Aided Mol. Des.* 10:11–22. Peptides of the form Ac-CXPGXC-NMe (SEQ ID. NO. 11) were evaluated by measurement of disulfide exchange equilibria, which indicated turn preferences between peptides of as much as 1 kcal/mol. Milburn et al. (1987) *J. Am. Chem. Soc.* 109:4486–4496.

An eleven-residue cyclic peptide, CGVSRQGKPYC, (SEQ ID NO. 12) based on the gene 5 protein from M13 is stably structured in aqueous solution, as demonstrated by NMR analysis. The cyclic peptide adopts a structure that is quite similar to the corresponding protein loop. The authors claim that well-defined β-hairpin structure had not been previously reported for any unprotected disulfide-constrained cycle. Rietman et al. (1996) *Eur. J. Biochem.* 238:706–713. This peptide has a Val-Pro pair at the nonhydrogen-bonded sites nearest to the cysteines.

Disulfide-cyclized peptides from the hairpin region of a rabbit defensin have antibacterial activity exceeding (about 5 to 10-fold) that of the linear analogs. Circular dichroism spectroscopy indicates some non-random structure in phosphate buffer. The more potent peptide (CAGFMRIRGRIHPLCMRR) (SEQ ID NO: 13 ) has a Gly-Pro pair at the nonhydrogen-bonded sites nearest to the cysteines. Thennarasu & Nagaraj (1999) *Biochem. Biophys. Res. Commun.* 254:281–283.

Several peptides from the loops of domain 1 of human CD4 have been studied in Zhang et al. (1996) *Nature Biotechnology* 14:472–475; Zhang et al. (1997) *Nature Biotechnology* 15:150–154. In addition to a disulfide constraint, the authors have added exocyclic aromatic amino acids to the peptide termini. No evidence for structure is given, but one cyclic peptide was reported to antagonize both normal CD4 interactions and those involved in CD4-mediated cell entry by HIV.

Few examples exist of small peptides that form a stable tertiary structure without assistance from disulfide bonds or metal ions. Most natural peptides encompassing hairpins are mainly devoid of structure in water or form aggregates. Ramirez-Alvarado et al. (1997) *Protein Sci.* 6:162–147. A hairpin peptide derived from the B1 domain (the 41–56 residue fragment) of protein G (GB 1) has been reported to form a well-populated hairpin (about 50%) in water. Blanco et al.(1994) *Nat. Struct. Biol.* 1:584–590. The GB1 hairpin has four threonine residues at hydrogen-bonded sites in the strands, including one Thr-Thr cross-strand pair. This is generally believed to be an unfavorable pairing. In addition, there are Trp-Val and Tyr-Phe pairs at adjacent nonhydrogen-bonded sites that might interact to form a small hydrophobic core.

Analysis of hairpin sequences in crystal structures has allowed the de novo design of a series of β-hairpin peptides based on the BH8 peptide. Ramirez-Alvarado et al. (1996) *Nat. Struct. Biol.* 3:604–612. The target structure was a type I' turn flanked by three-residue strands. Arg-Gly sequences were added to the ends to improve solubility. One peptide was partially folded into a hairpin conformation (about 30%) as determined by NMR. The importance of inter-strand side chain-side chain interactions was indicated by replacement of certain strand residues with alanine. None of the alanine-substituted peptides showed any tendency to form a hairpin. The same authors reported a second series of experiments in which position i+1 of the turn was varied. Ramirez-Alvarado et al. (1997) *J. Mol. Biol.* 273:898–912. No peptide was more structured than the original sequence with Asn in the turn. A review describing this work suggested that adding Glu-Lys pairs to the termini of the model peptide may help to stabilize the hairpin. Ramirez-Alvarado et al. (1999) *Bioorg. Med. Chem.* 7:93–103.

A peptide comprising the N-terminal 17 residues of the globular protein ubiquitin has been shown to form a native-like hairpin in both aqueous methanol and water, albeit at low apparent population. Zerella et al. (1999) *Protein Sci.* 8:1320–1331. A recent study, Zerella et al. (2000) *Protein Sci.* 9:2142–2150, focused on the contributions to the stability of the isolated peptides by residues within the turn region. The data indicated that in a peptide where Thr at position 9 was replaced by Asp, U(1–17)T9D, the native conformation was stabilized significantly over that of the wild type sequence. The estimated population of the folded hairpin was only 64%. Moreover, as the authors noted, the structure of the folded state of U(1–17)T9D may be more dynamic than indicated by the final ensemble. The reason for the greater stability upon substitution of the turn residue remains uncertain.

It is an object of the present invention to provide a simple model system for displaying small peptides with stable hairpin structure and methods of using such a model system in constructing and screening constrained peptide libraries useful in biological and therapeutic applications.

SUMMARY OF THE INVENTION

The present invention is based on the surprising identification of a novel structure motif, the tryptophan zipper (trpzip), that enables the stabilization of hairpin structures in very short peptides. Some of the trpzip peptides showing stable tertiary structures have a minimum length of 10–12 amino acids. Therefore, in one aspect, the invention provides a minimal peptide scaffold having the newly identified stable trpzip motif, comprising a presented turn sequence flanked by two opposite strands with a defined backbone hydrogen-bonding pattern, each strand comprising at least two Trp residues at non-hydrogen-bonded positions. The four Trp residues from the two strands form two Trp-Trp pairs that constitute a cross-strand zipper-like motif with great structural stability. Significantly, the trpzip motif does not require any disulfide bonds.

In one aspect, the presented turn sequence comprises at least 4 amino acids. In another aspect, the presented turn sequence comprises at least 6 amino acids. In addition to the four Trp residues, the two flanking strands comprise other amino acids, preferably naturally occurring L-form amino acids. In one preferred embodiment, the peptide scaffold has a minimum length of 10 amino acids, with 4 amino acids as the presented turn sequence and 3 amino acids each for the flanking strands. In other preferred embodiments, additional residues are included in the strand region and/or the turn region of the scaffold. As such, some preferred peptide scaffolds comprise 12, 14, 16, 18 or 20 amino acids. More preferably, the scaffold is no more than 20 amino acids in length.

The invention also encompasses libraries of structurally-constrained peptides, each peptide having the trpzip scaffold as described above, wherein the presented turn sequence consists of random amino acids. Methods of constructing such libraries are also contemplated. The subject libraries can be used for selecting novel peptides capable of binding to identified target molecules. Accordingly, the invention provides methods of identifying peptides capable of binding to a bioactive target molecule, comprising the steps of: a) providing a library of peptides comprising the novel trpzip scaffold; b) contacting the library with the target molecule; c) selecting from the library peptides capable of forming a noncovalent complex with the binding partner; and d) optionally isolating the peptides selected in step c). The selected peptides are useful per se as diagnostics or therapeutics (e.g., agonists or antagonists) used in treatment of biological organisms. Compositions and methods of the invention may also be useful in analyzing the structure-activity relationship of proteins of interest, thereby providing information for rational drug design.

DETAILED DESCRIPTION OF THE INVENTION

Figure 1:
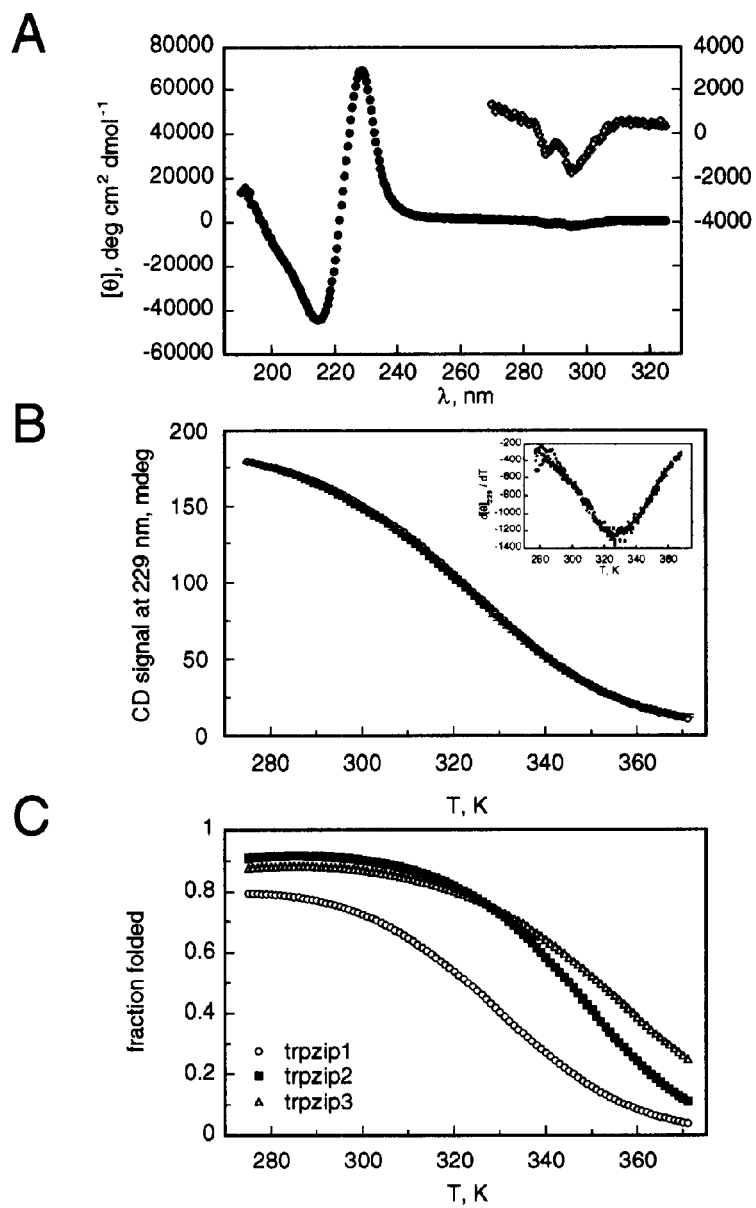
FIGS. 1A–1C are graphs showing the folding of trpzips 1–3. (1A) Circular dichroism (CD) spectrum of trpzip1. The near UV region is shown as an inset with a 10-fold expanded y-axis. (1B) Thermal denaturation of trpzip1 (20 $\mu$M) monitored by CD. The forward melting curve is shown as open circles, while the reverse melting curve is shown as the error bars associated with signal averaging during data acquisition. The first derivatives of melting curves (20, 50, 100, and 150 $\mu$M peptide) are overlaid in the inset. (1C) Temperature dependence of folding for trpzips1–3 (calculated from the thermodynamic parameters listed in Table 2).

The design of peptides that have well-defined tertiary structures tests our understanding of the principles governing the folding of larger proteins. Short peptides with significant hairpin structure have recently emerged as β-sheet model systems. In a separate study, the inventors of the present invention have discovered that in a disulfide-cyclized β-hairpin peptide, tryptophan was much more stabilizing in a non-hydrogen-bonded (NHB) strand position than other amino acids. Cochran et al. (2001) *J. Am. Chem. Soc.* 123:625–632. Paired, cross-strand NHB residues in the Cys-cyclized hairpin made roughly independent contributions to stability; thus, a single tryptophan-tryptophan cross-strand pair was shown to be highly stabilizing (and the best NHB residue pair identified). Cochran et al. WO 00/77194; Russell and Cochran (2000) *J. Am. Chem. Soc.* 122:12600–12601. The present invention provides a novel structural motif, the tryptophan zipper (trpzip), that greatly stabilizes the β-hairpin conformation in short peptides, without any disulfide bonds. As shown in the Examples, peptides having 12 or 16 amino acids in length with different turn sequences are monomeric and fold cooperatively in water. Surprisingly, the folding free energies of the trpzip peptides exceed substantially those of all previously reported β-hairpins and even those of some larger designed proteins. NMR structures of some of the exemplary trpzip peptides revealed exceptionally well-defined β-hairpin conformations stabilized by cross-strand pairs of indole rings. The peptides of the present invention are the smallest peptides to adopt an unique tertiary fold without requiring metal binding, unusual amino acids, or disulfide crosslinks.

Therefore, the present invention provides a novel peptide scaffold for β-turn display. By "scaffold", "peptide scaffold" or "protein scaffold" is meant an amino acid framework useful for presenting a peptide of interest, in a way that the peptide of interest is accessible to other molecules. Preferably, the peptide scaffold has stable, defined tertiary structure, such that the presented peptide adopts a constrained conformation for display.

The term "β-turn" or "β-hairpin", as used herein, refers to an antiparallel β-sheet structure comprising a turn region flanked by two opposite strands with defined backbone hydrogen-bonding pattern. There are several types of hairpins depending on the types of turn, including for example, types I, I', II, and II'. A "presented turn sequence" refers to the central subset region of a β-turn that forms the actual turn structure. As used herein, the term represents a segment with variable amino acid residues that is to be presented in a combinatorial library display. The segment is used to present randomized residues in searching for sequences exhibiting binding affinities to other target molecules of interest. For example, the presented turn sequences can be sequences capable of serving as substrates or inhibitors, being recognized by antibodies, binding to receptors or ligands, or being useful in column affinity chromatography. Using well known methods such as those further described below, such presented sequences can be identified and isolated for further studies and uses.

The term "tryptophan zipper" or "trpzip" refers to a "zipper-like" peptide motif characterized by four tryptophan residues capable of forming two Trp-Trp cross-strand pairs and stabilizing a β-hairpin tertiary structure. The Trp residues within a trpzip are located at non-hydrogen-bonded positions of the opposite strands.

"A defined backbone hydrogen-bonding pattern" as used herein refers to a tertiary structure with defined conformation that is formed and stabilized by interstrand hydrogen bonding participated by amide and/or carboxyl moieties of individual strand residues. "Non-hydrogen-bonded positions" or "NHB positions" as used herein refers to strand positions within the hairpin scaffold that do not contribute to and participate in the hydrogen-bonding pattern. See Sibanda et al. (1989) *J. Mol. Biol.* 229:759–777 for further description of the hydrogen-bonding patterns of β-hairpins and their nomenclature.

The scaffold of the present invention comprises at least two Trp—Trp NHB cross-strand pairs. The combination of at least two Trp-Trp NHB cross-strand pairs greatly stabilizes β-hairpin structures. As further disclosed in the Examples, several trpzip variants having different turn sequences are highly water-soluble, well-structured, and monomeric. High-resolution NMR structures of the peptides show the two cross-strand Trp pairs interdigitating in a zipper-like motif on the surface of the folded peptide. This arrangement of the indole side chains confers unusual spectroscopic properties on the folded molecules, and folding can therefore be monitored readily by changes in circular dichroism (CD) signal. The stabilities of the tryptophan zippers are significantly higher than those reported for other small β-structures. Indeed, on a per-residue basis, the tryptophan zippers have stabilities comparable to much larger native protein domains.

The scaffolds of the invention are non-cysteine constrained. In other words, the scaffolds do not require the involvement of disulfide bridges between strands in order to maintain the stability of the tertiary structures. As such, trpzip peptides of the invention are particularly useful in applications where the disulfide bond formation is either undesirable or unfavorable. For example, the trpzip scaffold can be used for the intracellular display of peptides.

The trpzip peptides of the invention are among the smallest peptides to adopt an unique and stable tertiary fold without requiring metal binding, unusual amino acids, or disulfide bridges. Previous studies have suggested that the minimal size of a stable protein domain without cysteine bridges is approximately 50 amino acids. Nygren and Uhlen (1997) *Curr. Opin. Struct. Biol.* 7:463–469; Privalov and Gill (1988) *Adv. Protein Chem.* 39:191–243. Because of their small size, unusual stability, and very favorable spectroscopic properties, the trpzip scaffolds of the invention provide a useful and simple system for the study and display of β-turns.

The invention provides a library of trpzip peptides for turn display. Preferably, the presented turn sequence consists of random amino acids. Randomization of the turn sequences can be achieved by using methods and techniques well known in the art. Generally, at least 2, preferably at least 4, more preferably at least 6, even more preferably at least 10 amino acid positions need to be randomized. In a preferred embodiment, the random peptide sequence is provided by oligonucleotide synthesis using randomized codon assignments. It should be realized, however, that in a library system encoded by random nucleotides, codons encoding stop signals (i.e., TAA, TGA and TAG) may be undesirably introduced into the structure. For example, in a synthesis with NNN as the random region, there is a 3/64 chance that the codon will be a stop codon. Thus, in a region of 10 residues, there is a likelihood that 46.7% of the peptides will prematurely terminate. In order to alleviate this problem, random residues can be encoded, for example, as NNK or NNS instead, where K=T or G; and S=C or G. This allows for encoding of all potential amino acid (changing their relative representation slightly), yet preventing the encoding of two stop residues TAA and TGA.

In a preferred embodiment, the peptide library is "fully randomized," meaning there are no sequence preferences or fixed residues at any position within the turn region. In another preferred embodiment, the library is randomized with bias. That is, some positions within the region are either held constant, or selected from a limited number of possibilities. For example, in a preferred embodiment, the residues are randomized within a defined category, such as of hydrophobic residues, hydrophilic residues, aliphatic residues, unbranched residues, branched residues, or aromatic residues, etc. In a preferred embodiment, the random residues are biased to β-turn formation. In addition to random residues in the turn regions, the invention also encompasses amino acid variations at strand positions of the scaffold, other than those occupied by the core Trp residues. For example, variations can occur at NHB strand sites and/or hydrogen-bonded strand sites. A position and its cross-strand pairing partner can have the same or different residues.

Many methods for generating peptide libraries are known in the art and can be used to generate the libraries of the invention. In one embodiment, members of the peptide library can be created by split-synthesis performed on a solid support such as polystyrene or polyacrylamide resin, as described by Lam et al. (1991) *Nature* 354:82 and PCT publication WO 92/00091. In another embodiment, the trpzip scaffold of the invention can be used in constructing and displaying intracellular peptide libraries.

A preferred method of generating the library of the present invention is phage display. Bacteriophage (phage) display is a known technique by which variant polypeptides are displayed as fusion proteins to the coat protein on the surface of bacteriophage particles (Scott, J. K. and Smith, G. P. (1990) *Science* 249: 386). A "phagemid" is a plasmid vector having a bacterial origin of replication, e.g., ColE1, and a copy of an intergenic region of a bacteriophage. The phagemid may be based on any known bacteriophage, including filamentous bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous peptide gene as a gene fusion such that the heterologous peptide is displayed on the surface of the phage particle.

The term "coat protein" means a protein, at least a portion of which is present on the surface of the virus particle. From a functional perspective, a coat protein is any protein which associates with a virus particle during the viral assembly process in a host cell, and remains associated with the assembled virus until it infects another host cell. The coat protein may be the major coat protein or may be a minor coat protein. A "major" coat protein is a coat protein which is present in the viral coat at 10 copies of the protein or more. A major coat protein may be present in tens, hundreds or even thousands of copies per virion.

A "fusion protein" is a polypeptide having two portions covalently linked together, where each of the portions is a polypeptide having a different property. The property may be a biological property, such as activity in vitro or in vivo. The property may also be a simple chemical or physical property, such as binding to a target molecule, catalysis of a reaction, etc. The two portions may be linked directly by a single peptide bond or through a peptide linker containing one or more amino acid residues. Generally, the two portions and the linker will be in reading frame with each other.

In one preferred embodiment, the trpzip peptides are fused to at least a portion of a phage coat protein to form a fusion protein. The fusion protein can be made by expressing a gene fusion encoding the fusion protein using known techniques of phage display such as those described below. The fusion protein may form part of a phage or phagemid particle in which one or more copies of the trpzip peptide are displayed on the surface of the particle. A gene comprising a nucleic acid encoding the trpzip peptide or the fusion protein are within the scope of the invention.

In another embodiment, the invention is a method comprising the steps of constructing a library containing a plurality of replicable expression vectors, each expression vector comprising a transcription regulatory element operably linked to a gene fusion encoding a fusion protein, wherein the gene fusion comprises a first gene encoding a trpzip peptide of the invention and a second gene encoding at least a portion of a phage coat protein, where the library comprises a plurality of genes encoding variant trpzip peptide fusion proteins. Variant first genes and libraries thereof encoding variant trpzip peptides are prepared using known mutagenesis techniques described in more detail below.

The invention also includes expression vectors comprising the fusion genes noted above, as well as a library of these vectors. The library of vectors may be in the form of a DNA library, a library of virus (phage or phagemid) particles containing the library of fusion genes or in the form of a library of host cells containing a library of the expression vectors or virus particles.

The invention also contemplates a method of selecting novel binding peptides capable of binding to a bioactive target molecule. By "binding peptide" as used herein is meant any peptide that binds with a selectable affinity to a target molecule. By "bioactive target molecule" as used herein is meant any molecule exerting any biological activity in vitro or in vivo, for which it is desirable to produce a ligand. Preferably, the target molecule is a protein. More preferably, the target molecules include receptors, hormone ligands, growth factors, antigens, antibodies, enzymes and enzyme substrates.

In a preferred embodiment, the method of selecting novel binding peptides comprises the steps of: (a) constructing a library of variant replicable expression vectors comprising a transcription regulatory element operably linked to a gene fusion encoding a fusion protein wherein the gene fusion comprises a first gene encoding the trpzip peptide, and a second gene encoding at least a portion of a phage coat protein, where the variant expression vectors comprise variant first genes; (b) transforming suitable host cells with the vectors; (c) culturing the transformed host cells under conditions suitable for forming recombinant phage or phagemid virus particles containing at least a portion of the expression vector and capable of transforming the host, so that the particles display one or more copies of the fusion protein on the surface of the particle; (d) contacting the particles with a target molecule so that at least a portion of the particles bind to the target molecule; and (e) separating the particles that bind from those that do not. In the method of the invention, the phage coat protein is preferably the gene III or gene VIII coat protein of a filamentous phage such as M13. Further, preferably the culturing of the transformed host cells is under conditions suitable for forming recombinant phage or phagemid particles where the conditions are adjusted so that no more than a minor amount of phage or phagemid particles display one or more copies of the fusion protein on the surface of the particle (monovalent display).

The invention also includes a method of introducing structural bias into a phage-displayed library, using steps (a) through (e) described above. The invention further includes a method of selecting beta-hairpin forming peptide structures from a phage-displayed library, using steps (a) through (e) described above where the target is known to bind beta-hairpin peptide structures, preferably a protein target known to so bind.

The utility of phage display lies in the fact that large libraries of selectively randomized protein variants (or randomly cloned cDNAs) can be rapidly and efficiently sorted for those sequences that bind to a target molecule with high affinity. Display of peptide (Cwirla et al. (1990) *Proc. Natl. Acad. Sci. USA* 87:6378) or protein (Lowman et al. (1991) *Biochemistry* 30:10832; Clackson et al. (1991) *Nature* 352: 624; Marks et al. (1991), *J. Mol. Biol.* 222:581; Kang et al. (1991) *Proc. Natl. Acad. Sci. USA* 88:8363) libraries on phage have been used for screening millions of polypeptides for ones with specific binding properties (Smith (1991) *Current Opin. Biotechnol.* 2:668). Sorting phage libraries of random mutants requires a strategy for constructing and propagating a large number of variants, a procedure for affinity purification using the target receptor, and a means of evaluating the results of binding enrichments.

Typically, variant polypeptides, such as the trpzip compounds of the invention, are fused to a gene III protein, which is displayed at one end of the virion. Alternatively, the variant polypeptides may be fused to the gene VIII protein, which is the major coat protein of the virion. Such polyvalent display libraries are constructed by replacing the phage gene III with a cDNA encoding the foreign sequence fused to the amino terminus of the gene III protein.

Monovalent phage display is a process in which a protein or peptide sequence is fused to a portion of a gene III protein and expressed at low levels in the presence of wild-type gene III protein so that particles display mostly wild-type gene III protein and one copy or none of the fusion protein (Bass et al. (1990) *Proteins* 8:309; Lowman, H. B. and Wells, J. A. (1991) *Methods: a Companion to Methods in Enzymology* 3:205). Monovalent display has the advantage over polyvalent phage display that progeny phagemid particles retain full infectivity. Avidity effects are reduced so that sorting is on the basis of intrinsic ligand affinity, and phagemid vectors, which simplify DNA manipulations, are used. One preferred phage display system is described in U.S. Pat. No. 5,821,047.

A two-step approach may be used to select high affinity ligands from peptide libraries displayed on M13 phage. Low affinity leads are first selected from naive, polyvalent libraries displayed on the major coat protein (protein VIII). The low affinity selectants are subsequently transferred to the gene III minor coat protein and matured to high affinity in a monovalent format.

Although most phage display methods have used filamentous phage, other phage display Systems, such as lambda phage, T4 phage and T7 phage display systems are also known and can be used to create a library of the trpzip peptides of the invention. WO 95/34683; U.S. Pat. No. 5,627,024; Ren et al. (1998) *Gene* 215:439; Zhu (1997) *CAN* 33:534; Jiang et al. (1997) *CAN* 128:44380; Ren et al. (1997) *CAN* 127:215644; Ren (1996) *Protein Sci.* 5:1833; Efimov et al. (1995) *Virus Genes* 10: 173; Smith & Scott (1993) *Methods in Enzymology* 217:228-257; U.S. Pat. No. 5,766,905.

Suitable gene III vectors for display of trpzip peptides of the invention include fUSE5 (Scott, J. K., and Smith G. P. (1990) *Science* 249:386–390); fAFF1 (Cwirla et al. (1990). *Proc. Natl. Acad. Sci. U.S.A.* 87:6378–6382); fd-CAT1 (McCafferty et al. (1990) *Nature* (London) 348:552–554); m663 (Fowlkes et al. (1992) *Biotechniques* 13:422–427); fdtetDOG, pHEN1 (Hoogenboom et al. (1991) *Nucleic Acids Res.* 19:4133–4137); pComb3 (Gram et al. (1992) *Proc. Natl. Acad. Sci. U.S.A.* 89:3576–3580); pCANTAB 5E (Pharmacia); and LamdaSurfZap (Hogrefe (1993)*Gene* 137:85–91).

Phage display methods for proteins, peptides and mutated variants thereof, including constructing a family of variant replicable vectors containing a transcription regulatory element operably linked to a gene fusion encoding a fusion polypeptide, transforming suitable host cells, culturing the transformed cells to form phage particles which display the fusion polypeptide on the surface of the phage particle, contacting the recombinant phage particles with a target molecule so that at least a portion of the particle bind to the target, separating the particles which bind from those that do not bind, are known and may be used with the method of the invention. See WO 97/29185; O'Boyle et al. (1997) *Virology* 236:338–347; Soumillion et al. (1994) *Appl. Biochem. Biotech.* 47:175–190; O'Neil and Hoess. (1995) *Curr. Opin. Struct. Biol.* 5:443–449; Makowski (1993) *Gene* 128:5–11; Dunn (1996) *Curr. Opin. Struct. Biol.* 7:547–553; Choo and Klug (1995) *Curr. Opin. Struct. Biol.* 6:431–436; Bradbury & Cattaneo (1995) *TINS* 18:242–249; Cortese et al., (1995) *Curr. Opin. Struct. Biol.* 6:73–80; Allen et al. (1995) *TIBS* 20:509–516; Lindquist & Naderi (1995) *FEMS Micro. Rev.* 17:33–39; Clarkson & Wells (1994) *Tibtech.* 12:173–184; Barbas (1993) *Curr. Opin. Biol.* 4:526–530; McGregor (1996) *Mol. Biotech.* 6:155–162; Cortese et al. (1996) *Curr. Opin. Biol.* 4:616–621; McLafferty et at. (1993) *Gene* 128:29–36.

The gene encoding the coat protein of the phage and the gene encoding the desired trpzip peptide portion of the fusion protein of the invention (i.e., the trpzip peptide of the invention fused to at least a portion of a phage coat protein) can be obtained by methods known in the art. The DNA encoding the gene may be chemically synthesized (Merrifield (1963) *J. Am. Chem. Soc.* 85:2149) and then mutated to prepare a library of variants as described below.

To ligate DNA fragments together to form a functional vector containing the gene fusion, the ends of the DNA fragments must be compatible with each other. In some cases, the ends will be directly compatible after endonuclease digestion. However, it may be necessary to first convert the sticky ends commonly produced by endonuclease digestion to blunt ends to make them compatible for ligation. To blunt the ends, the DNA is treated in a suitable buffer for at least 15 minutes at 15° C. with 10 units of the Klenow fragment of DNA polymerase I (Klenow) in the presence of the four deoxynucleotide triphosphates. The DNA is then purified by phenol-chloroform extraction and ethanol precipitation or other DNA purification technique.

The cleaved DNA fragments may be size-separated and selected using DNA gel electrophoresis. The DNA may be electrophoresed through either an agarose or a polyacrylamide matrix. The selection of the matrix will depend on the size of the DNA fragments to be separated. After electrophoresis, the DNA is extracted from the matrix by electroelution, or, if low-melting agarose has been used as the matrix, by melting the agarose and extracting the DNA from it, as described in sections 6.30–6.33 of Sambrook et al.

The DNA fragments that are to be ligated together (previously digested with the appropriate restriction enzymes such that the ends of each fragment to be ligated are compatible) are put in solution in about equimolar amounts. The solution will also contain ATP, ligase buffer and a ligase such as T4 DNA ligase at about 10 units per 0.5 µg of DNA. If the DNA fragment is to be ligated into a vector, the vector is at first linearized by cutting with the appropriate restriction endonuclease(s). The linearized vector is then treated with alkaline phosphatase or calf intestinal phosphatase. The phosphatasing prevents self-ligation of the vector during the ligation step.

After ligation, the vector with the foreign gene now inserted is purified and transformed into a suitable host cell. A preferred transformation method is electroporation. Electroporation may be carried out using methods known in the art. More than one (a plurality) electroporations may be conducted to increase the amount of DNA which is transformed into the host cells. Repeated electroporations are conducted as described in the art. See, for example, Vaughan et al. (1996) *Nature Biotechnology* 14:309–314. The number of additional electroporations may vary as desired from several (2,3,4, ... 10) up to tens (10, 20, 30, ... 100) and even hundreds (100, 200, 300, ... 1000). Repeated electroporations may be desired to increase the size of a combinatorial library, e.g. an antibody library, transformed into the host cells.

Preferably, for library construction, the DNA is present at a concentration of 25 micrograms/ml or greater. More preferably, the DNA is present at a concentration of about 30 micrograms/ml or greater, more preferably at a concentration of about 70 micrograms/ml or greater and even more preferably at a concentration of about 100 micrograms/ml or greater even up to several hundreds of micrograms/ml. Generally, the electroporation will utilize DNA concentrations in the range of about 50 to about 500 micrograms/ml. A time constant during electroporation greater than 3.0 milliseconds (ms) results in a high transformation efficiency.

The DNA is preferably purified to remove contaminants. The DNA may be purified by any known method, however, a preferred purification method is the use of DNA affinity purification. The purification of DNA, e.g., recombinant plasmid DNA, using DNA binding resins and affinity reagents is well known and any of the known methods can be used in this invention (Vogelstein, B. and Gillespie, D. (1979) *Proc. Natl. Acad. Sci. USA* 76:615; Callen, W. (1993) *Strategies* 6:52–53). Commercially available DNA isolation and purification kits are also available from several sources including Stratagene (CLEARCUT Miniprep Kit), and Life Technologies (GLASSMAX DNA Isolation Systems). Non-limiting examples of suitable methods for DNA purification include column chromatography, the use of hydroxylated silical polymers, rehydrated silica gel, boronated silicates, modified glass fiber membranes, fluorinated adsorbents, diatomaceous earth, dialysis, gel polymers and the use of chaotropic compounds with DNA binding reagents, all of which are known and widely used in the art. After purification, the DNA is eluted or otherwise resuspended in water, preferably distilled or deionized water, for use in electroporation at the concentrations of the invention. The use of low salt buffer solutions is also contemplated.

Any suitable cells which can be transformed by electroporation may be used as host cells in the method of the present invention. Suitable host cells which can be transformed include gram negative bacterial cells such as *E. coli*. Suitable *E. coli* strains include JM101, *E. coli* K12 strain 294 (ATCC number 31,446), *E. coli* strain W3110 (ATCC number 27,325), *E. coli* X1776 (ATCC number 31,537), *E. coli* XL-1Blue (Stratagene), and *E. coli* B; however many other strains of *E. coli*, such as XL1-Blue MRF', SURE, ABLE C, ABLE K, WM1100, MC1061, HB101, CJ136, MV1190, JS4, JS5, NM522, NM538, and NM539, may be used as well. Cells are made competent using known procedures.

Cell concentrations of about $10^{10}$ colony forming units (cfu)/mL of viable living cells and greater are preferably used for electroporation. More preferably, the viable cells are concentrated to about $1\times10^{11}$ to about $4\times10^{11}$ cfu/mL. Preferred cells which may be concentrated to this range are the SS320 cells described below. Cells are preferably grown in culture in standard culture broth, optionally for about 6–48 hrs (or to $OD_{600}$=0.6–0.8) at about 37° C., and then the broth is centrifuged and the supernatant removed (e.g. decanted). Initial purification is preferably by resuspending the cell pellet in a buffer solution (e.g. HEPES pH 7.4) followed by recentrifugation and removal of supernatant. The resulting cell pellet is resuspended in dilute glycerol (e.g. 5–20% v/v) and again centrifuged to form a cell pellet and the supernatant removed. The final cell concentration is obtained by resuspending the cell pellet in water or dilute glycerol to the desired concentration.

A particularly preferred recipient cell for the electroporation is a competent *E. coli* strain containing a phage F' episome. Any F' episome which enables phage replication in the strain may be used in the invention. Suitable episomes are available from strains deposited with ATCC or are commercially available (CJ236, CSH18, DH5alphaF', JM101, JM103, JM105, JM107, JM109, JM110), KS1000, XL1-BLUE, 71–18 and others). Strain SS320 was prepared by mating MC1061 cells with XL1-BLUE cells under conditions sufficient to transfer the fertility episome (F' plasmid) of XL1-BLUE into the MC1061 cells. In general, mixing cultures of the two cell types and growing the mixture in culture medium for about one hour at 37° C. is sufficient to allow mating and episome transfer to occur. The new resulting *E. coli* strain has the genotype of MC1061 which carries a streptomycin resistance chromosomal marker and the genotype of the F' plasmid which confers tetracycline resistance. The progeny of this mating is resistant to both antibiotics and can be selectively grown in the presence of streptomycin and tetracycline. Strain SS320 has been deposited with the American Type Culture Collection (ATCC), 10801 University Boulevard, Manassas, Va., USA on Jun. 18, 1998 and assigned Deposit Accession No. 98795.

This deposit of strain SS320 was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The organisms will be made available by ATCC under the terms of the Budapest Treaty, and subject to an agreement between Genentech, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the cultures on deposit should die or be lost or destroyed when cultivated under suitable conditions, they will be promptly replaced on notification with a viable specimen of the same culture. Availability of the deposited cultures is not to be construed as a license to practice the invention in contravention of the rights granted under the authority of any government in accordance with its patent laws.

A useful method for identification of certain residues or regions of the peptide that are preferred locations for mutagenesis is called "alanine scanning mutagenesis" as described by Cunningham and Wells (1989) *Science* 244:1081–1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with target molecule. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed peptides are screened for the desired activity.

Oligonucleotide-mediated mutagenesis is a preferred method for preparing the substitution, deletion, and insertion variants of the invention. This technique is well known in the art as described by Zoller et al. (1987) *Nucleic Acids Res.* 10: 6487–6504. Briefly, a gene encoding a protein fusion or heterologous polypeptide is altered by hybridizing an oligonucleotide encoding the desired mutation to a DNA template, where the template is the single-stranded form of the plasmid containing the unaltered or native DNA sequence of the gene. After hybridization, a DNA polymerase is used to synthesize an entire second complementary strand of the template which will thus incorporate the oligonucleotide primer, and will code for the selected alteration in the gene. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (1978) *Proc. Nat'l. Acad. Sci. USA* 75: 5765.

The DNA template is generated by those vectors that are derived from the bacteriophage used in the phage display system, e.g. bacteriophage M13 vectors (the commercially available M13mp18 and M13mp19 vectors are suitable), or those vectors that contain a single-stranded phage origin of replication; examples are described by Viera et al. (1987) *Meth. Enzymol.* 153:3. Thus, the DNA that is to be mutated can be inserted into one of these vectors in order to generate single-stranded template.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of the gene, and the other strand (the original template) encodes the native, unaltered sequence of the gene. This heteroduplex molecule is then transformed into a suitable host cell, usually a prokaryote such as *E. Coli* JM101. After growing the cells, they are plated onto agarose plates and screened using the oligonucleotide primer radiolabelled with 32-Phosphate to identify the bacterial colonies that contain the mutated DNA.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

Mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, other alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

Cassette mutagenesis is also a preferred method for preparing the substitution, deletion, and insertion variants of the invention. The method is based on that described by Wells et al. (1985) *Gene* 34:315. The starting material is a plasmid (or other vector) containing the gene to be mutated. The codon(s) in the gene to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the gene. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated DNA sequence of the gene. Vectors containing the mutated variants can be transformed into suitable host cells as described above.

PCR mutagenesis is also suitable for making amino acid sequence variants of the starting polypeptide. See Higuchi, in *PCR Protocols*, pp.177–183 (Academic Press, 1990); and Vallette et al., *Nuc. Acids Res.* 17:723–733 (1989). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

The transformed cells are generally selected by growth on an antibiotic, commonly tetracycline (tet) or ampicillin (amp), to which they are rendered resistant due to the presence of tet and/or amp resistance genes in the vector.

Suitable phage and phagemid vectors for use in this invention include all known vectors for phage display. Additional examples include pComb8 (Gram et al. (1992) *Proc. Natl. Acad. Sci. USA* 89:3576–3580); pC89 (Felici et al. (1991) *J. Mol. Biol.* 222:310—310); pIF4 (Bianchi et al. (1995) *J. Mol. Biol.* 247:154–160); PM48, PM52, and PM54 (Iannolo. (1995) *J. Mol. Biol* 248:835–844); fdH (Greenwood et al. (1991) *J. Mol. Biol.* 220:821–827); pfd8SHU, pfd8SU, pfd8SY, and fdISPLAY8 (Malik & Perham (1996) *Gene* 171:49–51); "88" (Smith (1993) *Gene* 128:1–2); f88.4 (Zhong et al. (1994) *J. Biol. Chem,* 269:24183–24188); p8V5 (Affymax); MB1 MB20, MB26, MB27, MB28, MB42, MB48, MB49, MB56: (Markland et al. (1991) *Gene* 109:13–19). Similarly, any known helper phage may be used when a phagemid vector is employed in the phage display system. Examples of suitable helper phage include M13-KO7 (Pharmacia), M13-VCS (Stratagene), and R408 (Stratagene).

After selection of the transformed cells, these cells are grown in culture and the vector DNA may then be isolated. Phage or phagemid vector DNA can be isolated using methods known in the art, for example, as described in Sambrook et al., *Molecular Cloning: A Laboratory Manual,* 2nd edition, (1989) Cold Spring Harbor Laboratory Press, Cold Spring Harbor, N.Y.

The isolated DNA can be purified by methods known in the art. This purified DNA can then be analyzed by DNA sequencing. DNA sequencing may be performed by the method of Messing et al. (1981) *Nucleic Acids Res.* 9:309, the method of Maxam et al. (1980) *Meth. Enzymol.* 65:499, or by any other known method.

Various aspects and embodiments of the present invention demonstrate the advantages of a novel model system for rationally designing and analyzing peptides of defined structural features. The combinatorial libraries comprising such peptides and methods of using thereof provide useful information and tools for exploring the basic structure-activity relationships involved in almost all biological molecular interactions. The peptides disclosed herein or generated according to the disclosure of the invention can be candidates for various biological or therapeutic agents, including but not limited to, enzyme inhibitors, ligand antagonists, ligand agonists, toxins, and immunogens.

In one aspect, the trpzip scaffold is used to present random peptide sequences to potential target molecules. Target molecules can be at least a portion of any molecules, including any known or unknown peptides, proteins, other macromolecules or chemical compounds that are capable of binding to the peptides and optionally exerting bioactivities. Protein molecules such as receptors, ligands, antigens, antibodies, enzymes, enzyme substrates and inhibitors, and fragments or portions thereof are encompassed by "target molecules." Other non-protein chemical compounds, organic or inorganic, can also be the target molecules of the peptides.

In another aspect, the sequence of an identified trpzip peptide is used to generate more candidate peptides. For example, the sequence may be the basis of subsequent round(s) of (biased) randomization, to develop peptides with desired activities. Alternatively, the identified sequence of the randomized region can be introduced into other peptide scaffold structures to obtain a display with different conformation/shape.

In one aspect, the system provided herein is used to screen for target molecules that bind to the random trpzip peptides. Furthermore, the trpzip peptides that bind to a target molecule with desirable bioactivities can be used to mimic or antagonize the functions of wild type ligand(s) of the identified target molecule.

The trpzip peptides or their binding partner molecules can also be used to generate antibodies for diagnostic and/or therapeutic uses. Methods of making antibodies to identified polypeptides and proteins are known in the art.

The following examples are provided by way of illustration and not by way of limitation. All disclosures of the references cited herein are expressly incorporated herein by reference in their entirety.

EXAMPLES

Example 1

Design and Characterization of Trpzip1 and Turn Variants Thereof

Methods

Peptide Synthesis

For all the examples described herein below, peptides were synthesized as C-terminal amides using standard Fmoc chemistry on a Pioneer synthesizer (PE Biosystems). Synthesized peptides were cleaved from resin by treatment with 5% triisopropylsilane in trifluoroacetic acid (TFA) for 1.5–4 hours at room temperature. After removal of TFA by rotary evaporation, peptides were precipitated by addition of ethyl ether and then purified by reversed-phase HPLC (acetonitrile/H$_2$O/0.1% TFA). Peptide identity was confirmed by electrospray mass spectrometry.

CD Spectroscopy and Analysis of Thermal Denaturation Curves

Spectra were acquired with an Aviv Instruments, Inc. Model 202 spectrophotometer. Peptide concentrations were determined spectrophotometrically as described in Gill & von Hippel (1989) Anal. Biochem. 182:319–326. Melting curves were acquired at 229 nm with 1.5 min equilibration at each temperature and an averaging time of 15 s. Thermal denaturation was reversible, as judged by recovery of CD signal ($\geq$95%) upon cooling. In addition, reverse melting curves were acquired for trpzips 1 and 4. Reverse and forward curves were identical in shape, with $\leq$0.5 K shift in $T_m$. As a model for the unfolded state of the peptides, the melting curve (linear) of an equimolar mixture of the trpzip1 half peptides SWTWEG (SEQ ID NO. 14) and NKWTWK (SEQ ID NO. 15) was measured. Data for the trpzip peptides were then fit to a two-state unfolding equilibrium as described in Minor & Kim (1994) Nature 367:660–663, fixing the unfolded baseline. Folded baselines, $T_m$, $\Delta H_m$ ($\Delta H$ at $T_m$), and $\Delta C_p$ were allowed to vary. For trpzips 5 and 6, the unfolded baseline could be fit directly to the experimental data. $\Delta S_m$ was calculated from the fit parameters ($\Delta H_m$/$T_m$). Errors in Table 2 were generated by the fitting algorithm (Kaleidagraph, Synergy Software) and were given to indicate the quality of the fits to the particular experimental data set. However, when fitting different data sets, $\Delta H_m$ and $\Delta C_p$ values varied by ~10%, as is typical in thermal denaturation experiments. Becktel & Schellman (1987) Biopolymers 26:1859–1877

Fitting with $\Delta C_p$ fixed to 0 Muñoz et al. (1997) Nature 390:196–199; Honda et al. (2000) J. Mol. Biol. 295:269–278) resulted in significant overestimates of hairpin population at lower temperatures; this portion of the stability curve was especially sensitive to errors in $\Delta C_p$. Fitting the trpzip denaturation curves in this manner required large shifts in $T_m$ (~5–10 K higher than the minimum in a derivative plot) and generated fits of lower quality. In addition, van't Hoff plots showed clear curvature through the transition region, indicating a non-zero $\Delta C_p$. From our data on trpzips 4, 5 and 6, we can estimate $\Delta C_p$~200 cal mol$^{-1}$ K$^{-1}$ for the gb1 peptide, which is sufficient to explain the discrepancy between our population estimate for the gb1 hairpin and those previously reported (Munoz et al. (1997), supra; Honda et al. (2000), supra). Recently, a non-zero $\Delta C_p$ (~100 cal mol$^{-1}$ K$^{-1}$) was reported for the unfolding of a 12-residue hairpin related to gb1. Espinosa & Gellman (2000) Angew. Chem. Int. Ed. 39:2330–2333.

Analytical Ultracentrifugation

Samples (in 20 mM potassium phosphate, 150 mM KCl, pH 7.1; 277 K) were analyzed in a Beckman XL-A ultracentrifuge at rotor speeds of 40 and 55 krpm. Peptide concentration was monitored by absorbance at or near 290 nm. Data for both speeds and two initial peptide concentrations (60 and 200 $\mu$M, 11 data sets total per peptide) were fit simultaneously to a nonideal single species model using the program NONLIN. Johnson et al. (1981) Biophys. J. 36: 575–588.

Figure 2:
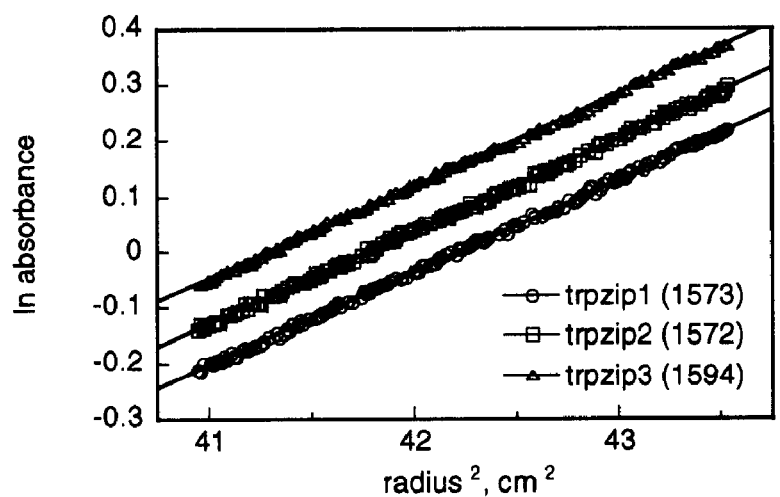
FIG. 2 is a graph depicting the equilibrium ultracentrifugation of trpzips 1–3. The data shown are for 60 $\mu$M peptide samples and a rotor speed of 40 krpm. Apparent molecular weights obtained from the slopes (assuming ideal behavior) are shown; calculated formula weights are 1608 for trpzips 1 and 2 and 1648 for trpzip3. Trpzip 1 data are offset vertically (In absorbance-0.085) for clarity.

Allowing nonideality improved the fit for the 200 $\mu$M samples while only slightly changing the reduced apparent molecular weight $\sigma$ (~+6%). For all 3 peptides, data from 60 $\mu$M samples fit an ideal model (FIG. 2) with random residuals. Expected $\sigma$ values were determined from partial specific volumes based on residue composition, calculated buffer density, and monomer formula weights.

NMR Spectroscopy and Structure Calculations

NMR samples contained 1–3 mM peptide in 92% H$_2$O/8% D$_2$O, pH 5.5 (trpzip1 and trpzip2) or pH 6.0 (trpzip4 and gb1, 41–56), with 0.1 mM DSS as a chemical shift reference. All spectra were acquired on a Bruker DRX-500 or a Varian Unity-400 spectrometer at 15° C. 2QF-COSY, TOCSY and ROESY spectra were acquired using gradient coherence selection or excitation sculpting for water suppression, as described in, for example, Cochran et al. (2001), supra, and references cited therein. Proton resonances were assigned by standard methods. Cochran et al. (2001), supra. $^3J_{H^N\text{-}H^\alpha}$ were obtained by fitting Lorentzian lines to the antiphase doublets of $H^N$-$H^\alpha$ peaks in 2QF-COSY spectra processed to high digital resolution in $F_2$. $^3J_{H^N\text{-}H^\alpha}$ were extracted from COSY-35 spectra acquired on $D_2O$ solutions of the peptides. Distance and dihedral angle restraints were generated as described in Skelton et al. (1994) *Biochemistry* 33:13581–13592. 80 initial structures were calculated using the hybrid distance geometry/simulated annealing program DGII (Havel et al. (1991) *Prog. Biophys. Mol. Biol.* 56:43–78.); 50 of these were further refined by restrained molecular dynamics using the AMBER all-atom forcefield implemented in DISCOVER as described previously (Skelton et al. (1994), supra). 20 structures having the lowest restraint violation energy and good geometry were chosen to represent the solution conformation of each peptide. The structure with the lowest r.m.s.d. to the average coordinates of the ensemble was chosen as the representative structure.

The concentration-dependence of the NMR spectra of trpzip2 and trpzip4 were evaluated by 1D $^1H$ NMR (10-fold and 100-fold dilution of samples used to acquire 2D data; final concentrations: 1.2 mM, 120 μM, and 12 μM for trpzip2, and 3.2 mM, 320 μM, and 32 μM for trpzip4). For both peptides, there were small chemical shift changes (in all cases $\Delta\delta \leq 0.08$ ppm between concentrated and 10-fold diluted samples, and $\Delta\delta \leq 0.02$ ppm between 10-fold and 100-fold diluted samples. For example, the trpzip2 peak with the largest $\Delta\delta$ was that from $W4^{H\epsilon3}$; in the 1.2 mM sample this proton resonates at 5.656 ppm (2.0 ppm upfield from the expected random coil position). This peak shifts 0.043 ppm downfield (120 μM sample), and an additional 0.004 ppm downfield upon further dilution (12 μM sample). In contrast, analytical ultracentrifugation indicates that trpzip2 is monomeric up to at least 200 μM. Taken together, these data imply that limited self-association may be occurring at millimolar concentrations. The fact that the $\Delta\delta$ are extremely small indicates that self-association does not significantly perturb the peptide structure; furthermore, there are no NOEs indicative of a specific interaction between monomers. Thus, the calculated structures accurately represent the monomer conformations.

Results

The peptide trpzip1 (Table 1) consists of a representative type II' turn sequence (EGNK) (SEQ ID NO. 16) flanked by the sequence WTW. An additional residue was added to each end of the peptide to permit cross-strand hydrogen bonding between the termini. Residues in hydrogen-bonded positions of the strands were taken from sequences used in our previous studies (WO 00/77194). Surprisingly, given that one-third of the residues are tryptophan, the peptide is freely soluble in water at millimolar concentrations. Trpzip1 has an unusual CD spectrum with intense exciton coupled bands at 215 and 229 nm (FIG. 1A), indicating interaction between the aromatic chromophores. Furthermore, the near UV CD spectrum of trpzip1 has well defined bands at the longer wavelength absorption maxima of tryptophan (FIG. 1A, inset), indicating that the indole side chains are in a defined chiral environment. In proteins, such near UV CD bands are often taken as evidence for fixed tertiary structure.

Trpzip1 has a reversible, cooperative thermal denaturation curve with a midpoint at 323 K (FIG. 1B). The data are of exceptionally high quality for a β-peptide: folding may be monitored sensitively at the 229 nm exciton coupled band, where sample absorbance causes few problems. Very poor signal-to-noise ratio is frequently a problem in CD-monitored folding studies of other small β-structures; see, for example, Kortemme et al. (1998) *Science* 281: 253–256. Reverse and forward melting curves overlay closely (FIG. 1B), demonstrating that the thermal transition is reversible. The melting temperature does not shift with peptide concentration (20–150 μM; FIG. 1B, inset), suggesting that trpzip1 does not self-associate at these concentrations. The thermal denaturation data fit well to a two-state model and reveal that folding is enthalpically favorable at ambient temperatures, with a significant heat capacity change (Table 2).

Two variants were synthesized, in which the Gly-Asn turn sequence of trpzip1 was replaced by stronger turn promoting sequences (trpzips 2 and 3; Table 1). Trpzip2 and trpzip3 have CD spectra that overlay closely with that of trpzip1 (not shown) and, likewise, exhibit reversible and cooperative melting behavior. Thermodynamic parameters for trpzips 2 and 3 are similar to those of trpzip1, with stability curves (and $T_m$) shifted to higher temperatures (FIG. 1C; Table 2). Interestingly, the denaturation curve for trpzip2 (Asn-Gly turn) is distinctly more cooperative than those of trpzips 1 or 3 (D-Pro-Asn turn). Trpzip2 also appears to be more stable than trpzip3 at low temperatures, despite previous conclusions that the D-Pro-Asn turn (and the related II' turn D-Pro-Gly) are more stabilizing than Asn-Gly. Cochran et al. (2001) *J. Am. Chem. Soc.* 123:625–632; Stanger & Gellman (1998) *J. Am. Chem. Soc.* 120:4236–4237; Syud et al. (1999) *J. Am. Chem. Soc.* 121:11577–11578. Instead, the conformational restriction of the D-proline appears to confer additional stability only at relatively high temperatures. Equilibrium ultracentrifugation confirms that all three trpzip peptides sediment as single species of the expected monomer molecular weights (FIG. 2; Table 2).

Figure 3:
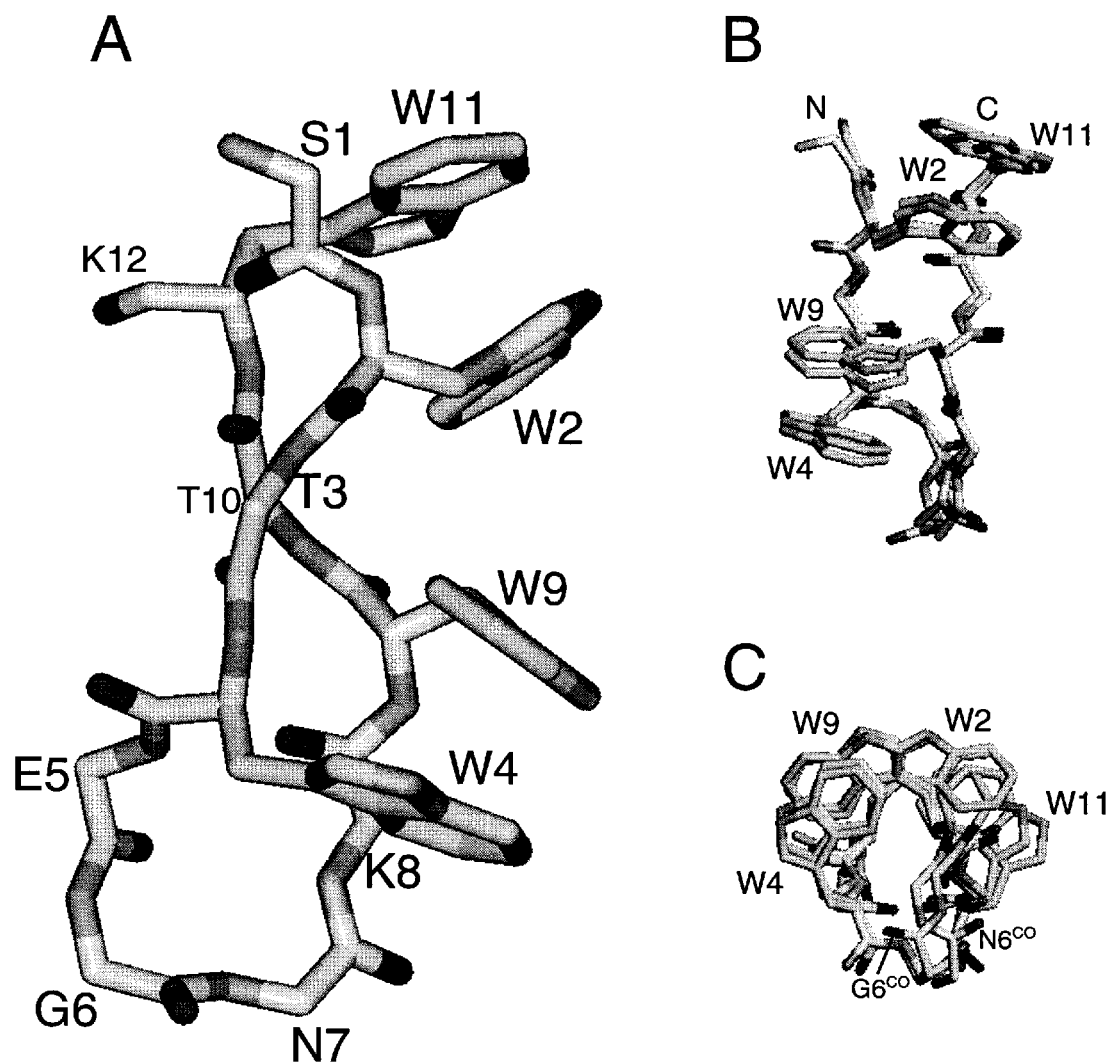
FIGS. 3A–3C depict NMR structures of trpzips 1 and 2. (3A) A representative structure of trpzip1 calculated based on NMR-derived restraints. The residues and their positions are indicated. (3B/3C) Representative structures of trpzips 1 and 2 aligned on the backbone atoms of residues 2–5 and 8–11 (r.m.s.d. of the mean coordinates of the aligned backbone atoms in the two ensembles is 0.37 Å); the view in 3C is rotated 90° relative to the view in 3B. The backbone carbonyl of residue 6 is indicated to emphasize the difference in turn geometry between the two structures (type II' for trpzip1 vs. type I' for trpzip2).

The three-dimensional structures of trpzip1 and trpzip2 were determined by NMR. All $^1H$ resonances were assigned by conventional 2D methods at 288K, pH 5.5. Resonance assignments and coupling constants for trpzips 1 and 2 are shown in Tables 5 and 6, respectively. 1D data are consistent with the peptides being predominantly monomeric at the millimolar concentrations used to acquire the 2D data; see above in Methods. Overall, the NMR data are of unusually high quality for short, linear peptides and provide strong evidence that the molecules are highly structured. The chemical shift dispersion is remarkable, allowing accurate measurement of the majority of $H^N$-$H^\alpha$ and $H^\alpha$-$H^\beta$ coupling constants and unambiguous assignment of nearly all NOE peaks; the number and intensity of observed NOE peaks are comparable to those routinely seen with small, stable proteins. Likewise, in addition to NOE-based distance restraints, numerous backbone dihedral angle restraints (derived from extreme $^3J_{H^N\text{-}H^\alpha}$) could be included in the structure calculations. Furthermore, the tryptophan sidechain conformations are all well defined, having $\chi_1$ angles of ~−60° (indicated by analysis of $^3J_{H^\alpha\text{-}H^\beta}$ and local ROEs). The high population of the folded state under the conditions of the NMR experiments, as well as the quality of the data, validate the high precision of the structures calculated for these peptides. Trpzip1 adopts a β-hairpin conformation with the expected type II' β-turn (FIG. 3A). Cross-strand tryptophan rings pack intimately against one another, with less contact between adjacent tryptophan pairs. Analysis of trpzip2 reveals a very similar structure, only deviating from trpzip1 by having a type I' β-turn at residues 6 and 7 (FIGS. 3B/3C; Table 3).

Example 2

Design and Characterization of GB1 Variants Containing the Trpzip Motif

The trpzip peptides may be compared to a previously described β-hairpin peptide taken from the B1 IgG-binding domain of protein G. The peptide gb1 (residues 41–56 of the B1 domain) exhibits partial hairpin character, estimated at ~40% (278 K) by NMR. Blanco et al. (1994) *Nature Struct. Biol.* 1:584–590. More recently, the estimated hairpin population has doubled, based on fluorescence-monitored folding studies and additional NMR experiments. Muñoz et al. (1997) *Nature* 390:196–199; Honda et al. (2000) *J. Mol. Biol.* 295: 269–278. The peptide appears to be stabilized by a cluster of four hydrophobic residues (W43, Y45, F52, and V54). From NOEs observed for the peptide, and from the structure of the sequence in the parent protein, the hydrophobic strand residues are expected to occupy adjacent non-hydrogen-bonded sites on one face of the hairpin. This is precisely the arrangement of tryptophan residues in the trpzip peptides, allowing the direct comparison of the gb1 and trpzip hydrophobic clusters.

Figure 4:
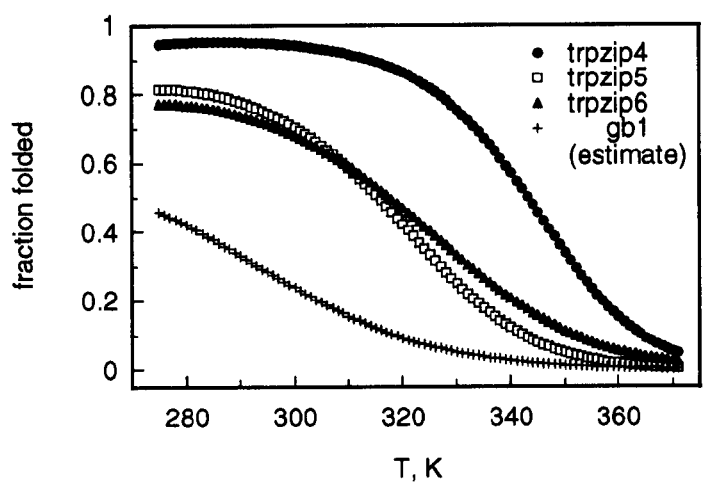
FIG. 4 is a graphic representation of the temperature dependence of folding for trpzips 4–6 (calculated from the thermodynamic parameters listed in Table 2). The estimated curve for gb1 was calculated by assuming that mutations in trpzip4 (i.e., those present in trpzips 5 and 6) have independent and additive effects on hairpin stability ($\Delta G_{unf, gb1} = \Delta G_{unf, trpzip5} - \{\Delta G_{unf, trpzip4} - \Delta G_{unf, trpzip}\}$) and is nearly identical in shape to previously reported gb I denaturation curves based on fluorescence or NMR measurements.

As expected from the stability of trpzips 1–3, replacement of gb1 residues Y45, F52, and V54 with tryptophan yields an exceptionally well-folded β-hairpin (trpzip4; Table 1). The thermal melting curve for trpzip4 is more cooperative than those of trpzips 1–3, yielding thermodynamic parameters that reflect this difference (Table 2). Trpzip4 is also more stable than trpzips 1–3 at low temperatures, resulting in a modest increase in folded population (FIGS. 1C and 4). Most importantly, the thermal denaturation curve of trpzip4 is much more cooperative than that of the wt gb1 peptide, and the melting temperature of trpzip4 is higher by at least 40 K, depending on the method used to estimate the folded population of gb1 (FIG. 4).

In contrast, when tryptophan residues 4, 9, and 11 of trpzip1 are replaced with the appropriate gb1 residues (Y, F, and V, respectively), we find no evidence by NMR for the hairpin conformation (all $^3J_{H^N-H^\alpha}<8$ Hz, not shown). This shows that the gb1 hydrophobic cluster is not sufficient to maintain a significant hairpin population without additional stabilizing elements.

To explore this in more detail, we reintroduced individually into trpzip4 the Phe-Tyr and Trp-Val cross-strand pairs of gb1 (trpzip5 and trpzip6, respectively). Unlike gb1, trpzips 5 and 6 each have one Trp-Trp cross-strand pair, so folding can be monitored by CD (229 nm, as for the other trpzips). We find both trpzip5 and trpzip6 to be much less stably folded than trpzip4 (Table 2; FIG. 4) but more stably folded than wildtype gb1. From our earlier studies in disulfide-cyclized hairpins, we expect ~1 kcal mol$^{-1}$ loss in stability for each gb1 cross-strand pair (Tyr-Phe or Trp-Val) relative to Trp-Trp. Russell & Cochran (2000) *J. Am. Chem. Soc.* 122:12600–12601. In agreement with this expectation, unfolding free energies (298 K) are 1.69, 0.57, and 0.49 kcal mol$^{-1}$ for trpzips 4, 5, and 6, respectively. Therefore, assuming additive stabilization from the two pairs, we estimate $\Delta G_{unf}$~–0.6 kcal mol$^{-1}$ for gb1 at 298 K. Our population estimate for gb1 agrees closely with the lower estimate originally reported. Blanco et al. (1994) *Nature Struct. Biol.* 1:584–590.

As observed for the other trpzip peptides, the NMR data for trpzip4 are of exceptional quality and support the conclusion that the molecule is well folded (Table 7). The fingerprint region of the trpzip4 COSY spectrum shows dramatic chemical shift dispersion, especially when compared to the spectrum for wildtype gb1 peptide (data not shown). Chemical shifts represent population-weighted averages of all conformations adopted in solution; therefore, the extreme $H^N$ and $H^\alpha$ shifts of trpzip4 indicate that the folded conformation is highly populated. From these data, taken together with the thermal denaturation curves (FIG. 4), we conclude that trpzip4 has a much higher folded population than the gb1 peptide and that the cross-strand tryptophan pairs of the trpzip motif are superior to the hydrophobic cluster of gb1.

Figure 5:
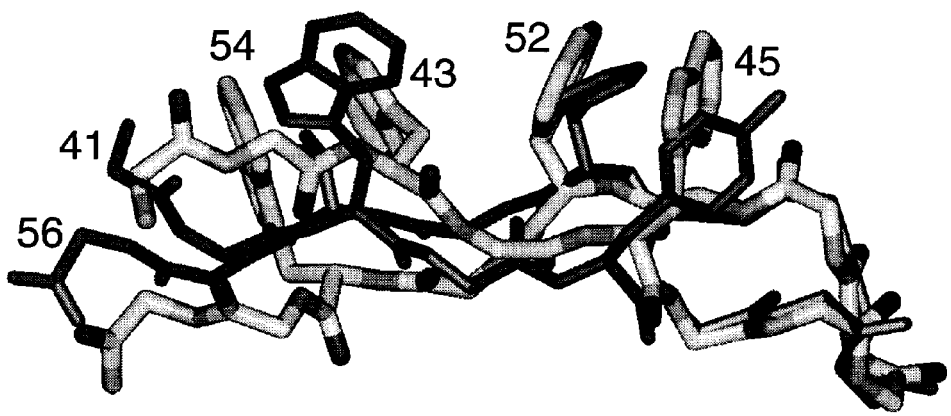
FIG. 5 compares NMR structures of trpzip4 (light grey) and gb1 protein (dark grey). The trpzip4 structure is a representative structure from the ensemble of 20 structures calculated based on NMR-derived restraints. The backbone atoms of gb1 protein residues 46–52 were superposed on the mean structure of the trpzip4, yielding an r.m.s.d. of 0.67 Å.
Figure 6:
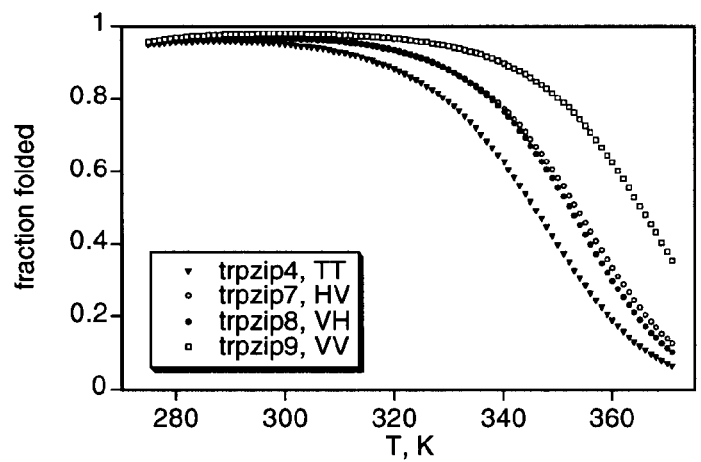
FIG. 6 is a graphic representation of the temperature dependence of folding for trpzips 4 and 7–9 (calculated from the thermodynamic parameters listed in Table 4).

The structure of trpzip4 shows Trp-Trp packing and strand orientations similar to those observed in trpzips 1 and 2 (Table 3; FIG. 5), despite the fact that there are six rather than four intervening turn residues. Trpzip4 extends the strands by another residue and presents a type I β-turn, with K50 adopting a positive φ angle. The turn geometry of trpzip4 is indistinguishable from that of the same turn in the full length B1 domain within the error of the structure determinations (FIG. 5). The twist of the two strands, however, is markedly different between the peptide and the protein; the protein is only modestly twisted (2GB1; Θ~20°), whereas trpzip4 is highly twisted (Θ~70°). This large twist is within the range observed in natural proteins and still allows good hydrogen-bonding geometry. The high degree of twist would appear to result from the cross-strand Trp-Trp packing, since it is observed in all three trpzip structures. The backbone coupling constants for tryptophan residues in the three peptides (7.1–8.2 Hz) are lower than those of the intervening hydrogen-bonded threonine residues (8.9–9.8 Hz), consistent with the alternating less and more negative φ angles that are a hallmark of a twisted sheet. Chothia (1983) *J. Mol. Biol.* 163:107–117. The geometry of the tryptophan zipper is that expected for an antiparallel β-coiled coil.

Example 3

Design and Characterization of Trpzip4 Variants with Improved Stabilities

Trpzips 1–6 described above consist of the core strand motif WTW paired with WTW on the opposite strand. Residues other than threonine may be possible at the hydrogen bonding sites in between the two Trp residues of each strand. To explore this, trpzips 7–9 (Table 1) were synthesized, in which the two threonines of trpzip4 are replaced by His-Val, Val-His, and Val-Val pairs, respectively. Trpzips 7–9 formed hairpin structures with CD spectra extremely similar to that shown in FIG. 1A for trpzip1. In addition, trpzips 7–9 are all more stable than trpzip4, as determined from thermal denaturation experiments (Table 4), demonstrating that these substitutions for threonine are fully compatible with the trpzip scaffold. Other similar residue substitutions are expected to be compatible as well, for example, Ile instead of Val; and Phe, Tyr, or Trp instead of His.

In conclusion, the trpzip peptides provided herein behave as folded proteins by generally accepted criteria. Presently, they are the smallest all-natural linear polypeptides having such folding behaviors. Their per-residue thermodynamic parameters ($\Delta G$, $\Delta H$, and $\Delta C_p$) are comparable to those of larger protein domains, indicating that, like other proteins, the folding of the trpzip hairpins is driven by burial of hydrophobic surface area (i.e., tryptophan sidechains). Alexander et al. (1992) *Biochemistry* 31:3597–3603; Becktel & Schellman (1987) *Biopolymers* 26:1859–1877.

TABLE 1

Sequences of trpzip and gb1 peptides

| | | | |
|---|---|---|---|
| trpzip1 | SWTWEGNKWTWK | (type II' turn) | (SEQ ID NO: 1) |
| trpzip2 | SWTWENGKWTWK | (type I' turn) | (SEQ ID NO: 2) |
| trpzip3 | SWTWEpNKWTWK | (type II' turn) | (SEQ ID NO: 3) |
| gb1, 41–56 | GEWTYDDATKTFTVTE | (type I turn) | (SEQ ID NO: 4) |
| trpzip4 | GEWTWDDATKTWTWTE | (gb1: Y45W, F52W, V54W) | (SEQ ID NO: 5) |
| trpzip5 | GEWTYDDATKTFTWTE | (gb1: V54W) | (SEQ ID NO: 6) |
| trpzip6 | GEWTWDDATKTWTVTE | (gb1: Y45W, F52W) | (SEQ ID NO: 7) |
| trpzip7 | GEWHWDDATKTWVWTE | | (SEQ ID NO: 8) |
| trpzip8 | GEWVWDDATKTWHWTE | | (SEQ ID NO: 9) |
| trpzip9 | GEWVWDDATKTWVWTE | | (SEQ ID NO: 10) |

All peptides were synthesized as C-terminal amides; p = D-proline.
Residue numbers for the gb1 peptide correspond to those of the parent 56-residue B1 domain.

TABLE 2

Thermal unfolding and sedimentation analysis of trpzip peptides

| parameter | trpzip1 | trpzip2 | trpzip3 | trpzip4 | trpzip5 | trpzip6 |
|---|---|---|---|---|---|---|
| $T_m$, K | 323.0 ± 0.3 | 345.0 ± 0.1 | 351.8 ± 0.2 | 343.1 ± 0.1 | 315.8 ± 0.2 | 317.7 ± 0.48 |
| $\Delta H_m$, cal mol$^{-1}$ | 10790 ± 120 | 16770 ± 60 | 13020 ± 70 | 21860 ± 60 | 13320 ± 140 | 10290 ± 300 |
| $\Delta S_m$, cal mol$^{-1}$ K$^{-1}$ | 33.4 | 48.6 | 37.0 | 63.7 | 42.2 | 32.4 |
| $\Delta C_p$, cal mol$^{-1}$ K$^{-1}$ | 231 ± 4 | 281 ± 2 | 195 ± 2 | 380 ± 4 | 325 ± 10 | 236 ± 17 |
| $\sigma_{obs}/\sigma_{calc}$* | 1.02 ± 0.04 | 1.01 ± 0.04 | 1.00 ± 0.04 | n.d.[†] | n.d. | n.d. |

Thermal melts were acquired with 20 μM peptide samples in 20 mM potassium phosphate, pH 7.0.
*σ = reduced apparent molecular weight, as determined from sedimentation data fit to a non-ideal single-species model (see Methods).
[†]n.d. = not determined; the thermal denaturation curve of trpzip4 was identical at five-fold higher peptide concentration (100 μM vs. 20 μM). Thermal unfolding parameters of ΔH = 11600 cal mol$^{-1}$ and ΔS = 39 cal mol$^{-1}$ K$^{-1}$ have been reported for the gb1 peptide, assuming ΔCp = 0.

TABLE 3

NMR structural statistics for trpzip peptides

| parameter | trpzip1 | trpzip2 | trpzip4 |
|---|---|---|---|
| R.m.s. deviation from exp'tal distance restraints (Å) (number of restraints) | 0.005 ± 0.001 (77) | 0.004 ± 0.003 (84) | 0.003 ± 0.001 (117) |
| R.m.s. deviation from exp'tal dihedral restraints (°) (number of restraints) | 0.14 ± 0.09 (15) | 0.16 ± 0.09 (15) | 0.33 ± 0.08 (21) |
| Maximum distance violation (Å) | 0.03 ± 0.00 | 0.04 ± 0.03 | 0.03 ± 0.01 |
| Maximum dihedral violation (°) | 0.5 ± 0.3 | 0.6 ± 0.3 | 1.1 ± 0.3 |
| Ramachandran geometry (% in most favored region)* | 71 ± 10 | 85 ± 10 | 82 ± 4 |
| Backbone (N, Cα, C) rmsd from mean coordinates (Å) (residues used for rmsd calculation) | 0.40 ± 0.07 (2–11) | 0.41 ± 0.09 (2–11) | 0.29 ± 0.06 (43–54) |

Resonance assignments and coupling constants for trpzip1, trpzip2, and trpzip4 are provided in Tables 5–7, respectively.
*Ramachandran geometry was evaluated using the program PROCHECK (Laskowski et al. (1993) J. Appl. Crystallogr. 26: 283–291); remainder of the residues for all structures are in the allowed regions of ϕ, ψ space, with none in the disallowed or generously allowed regions.

TABLE 4

Thermal unfolding analysis of trpzips 7–9

| parameter | trpzip7 | trpzip8 | trpzip9 |
|---|---|---|---|
| $T_m$, K | 353.4 ± 0.1 | 352.2 ± 0.1 | 365.1 ± 0.0 |
| $\Delta H_m$, cal mol$^{-1}$ | 25030 ± 100 | 25980 ± 110 | 26690 ± 80 |
| $\Delta S_m$, cal mol$^{-1}$ K$^{-1}$ | 70.8 | 73.8 | 73.1 |
| $\Delta C_p$, cal mol$^{-1}$ K$^{-1}$ | 418 ± 4 | 440 ± 4 | 402 ± 2 |

Thermal melts were acquired with 20 μM peptide samples in 20 mM potassium phosphate, pH 7.0.

TABLE 5

Resonance assignments and coupling constants for trpzip1 at 288K, pH 5.5

| Res | H$^N$ | H$^\alpha$ | H$^\beta$ | Other | $^3J_{H\alpha-H\beta}$ | $^3J_{HN-H\alpha}$ |
|---|---|---|---|---|---|---|
| 1 Ser | — | 3.40 | 3.69* | | NA | |
| 2 Trp | 8.81 | 5.20 | <u>3.02</u>, 3.13 | δ1 = 7.38; ε1 = 10.28; ε3 = 7.46; ζ2 = 7.37; ζ3 = 7.20; η2 = 7.26 | 11.5, 2.9 | NA |
| 3 Thr | 9.56 | 4.85 | 3.99 | γ = 1.12 | NA | 8.9 |
| 4 Trp | 8.92 | 4.61 | 2.07, <u>2.94</u> | δ1 = 6.96; ε1 = 9.80; ε3 = 5.49; ζ2 = 7.17; ζ3 = 6.45; η2 = 6.88 | 5.5, 10.9† | 7.9 |
| 5 Glu | 8.36 | 4.34 | 1.75, 1.87 | γ = 2.01, 2.09 | 7.0, 7.1 | 8.6 |
| 6 Gly | 8.21 | 3.48, 3.77 | | | | 6.7, 6.0 |
| 7 Asn | 8.14 | 3.93 | 2.74, 2.79 | δ = 6.83, 7.50 | NA | 8.4 |
| 8 Lys | 6.53 | 4.16 | 1.66, 1.72 | γ = 1.09, 1.24; δ = 1.60*; ε = 2.95* | NA | NA |
| 9 Trp | 8.55 | 5.17 | <u>2.95</u>, 3.27 | δ1 = 7.26; ε1 = 9.93; ε3 = 7.31; ζ2 = 7.22; ζ3 = 7.09; η2 = 7.17 | 10.6, 3.3 | 7.8 |
| 10 Thr | 9.77 | 4.86 | 4.00 | γ = 1.15 | NA | NA |
| 11 Trp | 9.00 | 4.26 | 2.01, <u>2.76</u> | δ1 = 6.80; ε1 = 10.02; ε3 = 5.31; ζ2 = 7.36; ζ3 = 6.58; η2 = 7.08 | 4.6, 12.3 | 7.4 |
| 12 Lys | 7.73 | 4.16 | <u>1.37</u>, 1.50 | γ = 1.14, 1.20; δ = 1.49*; ε = 2.78* | 9.8, 5.0 | 9.3 |
| 13 NH$_2$ | 6.69, 7.04 | | | | | |

Chemical shifts for the pro R protons of stereospecifically assigned methylene groups are underlined.
*indicates degenerate methylene protons.
NA indicates that the necessary peak was too overlapped or broad to determine an accurate value of the coupling constant.
†Note: assuming that the Hα-Hβ coupling constants are a weighted average resulting from the three low-energy χ1 rotamers (−60°, 180°, +60°), then values of 5.5 and 10.9 Hz in conjunction with analysis of local ROEs gives a population distribution for Trp4 χ1 with ratios −60°:180:+60° of approximately 3.5:1:0 [Kessler, H., Griesinger, C., & Wagner, K. (1987) J. Am. Chem. Soc. 109, 6927–6933]. An NOE between Trp4$^{H\zeta2}$ and Asn7$^{H\alpha}$ was observed that apparently arises from the small population with Trp4 χ1 = 180°; this NOE is inconsistent with the major −60° χ1 conformation and was removed from the structure calculation to avoid distortion of the turn geometry.

TABLE 6

Resonance assignments and coupling constants for trpzip2 at 288K, pH 5.5

| Res | H$^N$ | H$^\alpha$ | H$^\beta$ | Other | $^3J_{H\alpha-H\beta}$ | $^3J_{HN-H\alpha}$ |
|---|---|---|---|---|---|---|
| 1 Ser | — | 3.81 | 3.54* | | NA | |
| 2 Trp | 8.91 | 5.25 | <u>3.02</u>, 3.09 | δ1 = 7.39; ε1 = 10.25; ε3 = 7.44; ζ2 = 7.39; ζ3 = 7.23; ; η2 = 7.30 | 12.3, 3.1 | 8.0 |
| 3 Thr | 9.58 | 4.91 | 4.04 | γ = 1.15 | NA | 9.4 |
| 4 Trp | 8.89 | 4.67 | 2.01, 2.94 | δ1 = 6.86; ε1 = 9.91; ε3 = 5.66; ζ2 = 7.22; ζ3 = 6.55; η2 = 6.98 | 5.9, 10.7† | 7.9 |
| 5 Glu | 8.50 | 4.36 | 1.78, 1.93 | γ = 2.05, 2.13 | 6.2, 8.3 | 8.2 |
| 6 Asn | 9.24 | 4.19 | 2.65, 2.94 | δ = 6.97, 7.69 | 9.1, 6.1 | 6.4 |
| 7 Gly | 7.71 | 3.23, 3.82 | | | | 6.3, 4.8 |
| 8 Lys | 6.88 | 4.26 | 1.66, 1.72 | γ = 1.23, 1.28; δ = 1.67*; ε = 3.02* | 7.2, 5.1 | 8.7 |
| 9 Trp | 8.61 | 5.17 | <u>2.91</u>, 3.28 | δ1 = 7.21; ε1 = 9.81; ε3 = 7.26; ζ2 = 7.22; ζ3 = 7.09; η2 = 7.19 | 10.7, 4.0 | 7.1 |
| 10 Thr | 9.90 | 4.90 | 4.07 | γ = 1.21 | NA | 9.8 |
| 11 Trp | 9.06 | 4.27 | 1.95, <u>2.74</u> | δ1 = 6.82; ε1 = 10.07; ε3 = 5.25; ζ2 = 7.41; ζ3 = 6.60; η2 = 7.13 | 5.0, 12.5 | 7.9 |

TABLE 6-continued

Resonance assignments and coupling constants for trpzip2 at 288K, pH 5.5

| Res | $H^N$ | $H^\alpha$ | $H^\beta$ | Other | $^3J_{H\alpha-H\beta}$ | $^3J_{HN-H\alpha}$ |
|---|---|---|---|---|---|---|
| 12 Lys | 7.65 | 4.21 | 1.40, 1.51 | γ = 1.19, 1.25; δ = 1.55*; ε = 2.78, 2.85 | 9.7, 5.6 | 9.5 |
| 13 NH$_2$ | 6.70, 7.37 | | | | | |

Chemical shifts for the pro R protons of stereospecifically assigned methylene groups are underlined.
*indicates degenerate methylene protons.
NA indicates that the necessary peak was too overlapped or broad to determine an accurate value of the coupling constant.
†Note: assuming that the coupling constants are a weighted average resulting from the three low-energy χ1 rotamers (−60°, 180°, +60°), then values of 5.9 and 10.7 Hz in conjunction with analysis of local ROEs gives a population distribution for Trp4 χ1 with ratios −60°:180:+60° of approximately 3:1:0 [Kessler, H., Griesinger, C., & Wagner, K. (1987) J. Am. Chem. Soc. 109, 6927–6933]. An NOE between Trp4$^{H\zeta2}$ and Gly7$^{H\alpha1}$ was observed that apparently arises from the small population with Trp4 χ1 = 180°; this NOE is inconsistent with the major −60° χ1 conformation and was removed from the calculation to avoid distortion of the turn geometry.

TABLE 7

Resonance assignments and coupling constants for trpzip4 at 288K, pH 6.0

| Res | $H^N$ | $H^\alpha$ | $H^\beta$ | Other | $^3J_{H\alpha-H\beta}$ | $^3J_{HN-H\alpha}$ |
|---|---|---|---|---|---|---|
| 41 Gly | — | 3.11, 3.55 | | | | |
| 42 Glu | 7.38 | 4.31 | 1.77, 1.96 | γ = 1.96* | 6.0, 2.7 | 7.5 |
| 43 Trp | 8.46 | 5.36 | 3.06, 3.40 | δ1 = 7.25; ε1 = 9.79; ε3 = 7.60; ζ2 = 7.20; ζ3 = 7.23; η2 = 7.21 | 10.4, 1.9 | 8.4 |
| 44 Thr | 9.92 | 5.01 | 4.11 | γ = 1.21 | NA | 9.9 |
| 45 Trp | 9.05 | 4.24 | 1.71, 2.63 | δ1 = 6.87; ε1 = 10.28; ε3 = 4.97; ζ2 = 7.21; ζ3 = 6.27; η2 = 6.87 | 5.3, 12.1 | 7.2 |
| 46 Asp | 7.85 | 4.58 | 2.26, 2.63 | | 4.1, 12.0 | 9.9 |
| 47 Asp | 8.61 | 4.09 | 2.56, 2.69 | | 8.5, 6.9 | 5.6 |
| 48 Ala | 8.25 | 4.17 | 1.49 | | | 5.9 |
| 49 Thr | 7.11 | 4.17 | 4.20 | γ = 1.09 | NA | 9.2 |
| 50 Lys | 7.71 | 2.99 | 1.86, 2.17 | γ = 1.28, 1.38; δ = 1.75*; ε = 3.10* | 3.8, 12.1 | 7.5 |
| 51 Thr | 6.40 | 4.43 | 3.93 | γ = 1.10 | 5.3 | 8.8 |
| 52 Trp | 8.29 | 5.30 | 2.99, 3.38 | δ1 = 7.17; ε1 = 9.74; ε3 = 7.58; ζ2 = 7.10; ζ3 = 7.21; η2 = 7.18 | 10.8, 1.8 | 9.7 |
| 53 Thr | 9.80 | 5.00 | 4.07 | γ = 1.20 | NA | 9.8 |
| 54 Trp | 9.03 | 4.50 | 1.75, 2.71 | δ1 = 6.73; ε1 = 10.03; ε3 = 5.21; ζ2 = 7.25; ζ3 = 6.40; η2 = 6.95 | 4.7, 12.2 | 7.7 |
| 55 Thr | 8.16 | 4.26 | 3.89 | γ = 1.05 | 5.3 | 9.5 |
| 56 Glu | 8.39 | 3.88 | 1.87, 2.02 | γ = 2.30* | 8.9, 6.2 | 6.6 |
| 57 NH$_2$ | 7.12, 7.56 | | | | | |

Chemical shifts for the pro R protons of stereospecifically assigned methylene groups are underlined.
*indicates degenerate methylene protons.
NA indicates that the necessary peak was too overlapped or broad to determine an accurate value of the coupling constant.

While the invention has necessarily been described in conjunction with preferred embodiments, one of ordinary skill, after reading the foregoing specification, will be able to effect various changes, substitutions of equivalents, and alterations to the subject matter set forth herein, without departing from the spirit and scope thereof. Hence, the invention can be practiced in ways other than those specifically described herein.

What is claimed is:

1. An isolated trpzip peptide scaffold comprising a presented turn sequence flanked on one side by first flanking peptide and flanked on the other side by a second flanking peptide, wherein the first flanking peptide consists of an amino sequence WTW and the second flanking sequence consists of an amino acid sequence WTW;

wherein each of the T residues in each flanking peptide can be substituted with valine or isoleucine, or if the T residue on the first flanking peptide is substituted with valine or isoleucine, then the T on the second flaking peptide is substituted with H, F, Y or W, or if the T residue on the second flaking peptide is substituted with valine or isoleucine, then the T on the second flanking peptide is substituted with H, F, Y or W; wherein each of the W residues of the first and second flanking peptides is at a non-hydrogen bonded position and wherein each W residue on one of the flanking peptides forms a cross peptide pair with a W residue on the other flanking peptide and the peptide scaffold lacks a disulfide bond and comprises no more than 20 amino acids.

2. The peptide scaffold of claim 1, wherein the presented turn sequence comprises at least 4 amino acids.

3. The peptide scaffold of claim 2, wherein the presented turn sequence comprises at least 6 amino acids.

4. The peptide scaffold of claim 1, wherein each flanking strand consists of naturally occurring L-form amino acids.

5. The peptide scaffold of claim 1 comprising at least 12 amino acids.

6. The peptide scaffold of claim 1, wherein the presented turn sequence is a type I, type II, or type III turn sequence.

* * * * *

UNITED STATES PATENT AND TRADEMARK OFFICE
CERTIFICATE OF CORRECTION

PATENT NO. : 6,914,123 B2
DATED : July 5, 2005
INVENTOR(S) : Cochran et al.

It is certified that error appears in the above-identified patent and that said Letters Patent is hereby corrected as shown below:

Title page,
Item [56], References Cited, OTHER PUBLICATIONS,
"Barthe et al." reference, insert an open quotation before the word "Synthesis" and an end quotation after the word "bridges,"; and
"Bass et al." reference, "Phage An Enrichment" should read -- Phage: An Enrichment --.

Column 11,
Line 35, "*Biol.* 4:616-621; McLafferty et at. (1993)" should read -- *Biol.* 7:616-621; McLafferty et al. (1993) --.

Column 35,
Line 6, "amino sequence" should read -- amino acid sequence --.
Line 11, "second flaking" should read -- second flanking --.
Line 13, "second flaking peptide" should read -- second flanking peptide --.

Signed and Sealed this

Fifteenth Day of November, 2005

JON W. DUDAS
*Director of the United States Patent and Trademark Office*